(12) United States Patent
Pastine

(10) Patent No.: US 9,862,797 B2
(45) Date of Patent: Jan. 9, 2018

(54) STERICALLY HINDERED ALIPHATIC POLYAMINE CROSS-LINKING AGENTS, COMPOSITIONS CONTAINING THEM AND USES THEREOF

(71) Applicant: CONNORA TECHNOLOGIES, INC., Hayward, CA (US)

(72) Inventor: Stefan J. Pastine, San Francisco, CA (US)

(73) Assignee: Connora Technologies, Inc., Hayward, CA (US)

( * ) Notice: Subject to any disclaimer, the term of this patent is extended or adjusted under 35 U.S.C. 154(b) by 0 days.

(21) Appl. No.: 15/028,342

(22) PCT Filed: Oct. 14, 2014

(86) PCT No.: PCT/US2014/060524
§ 371 (c)(1),
(2) Date: Apr. 8, 2016

(87) PCT Pub. No.: WO2015/054698
PCT Pub. Date: Apr. 16, 2015

(65) Prior Publication Data
US 2016/0264717 A1 Sep. 15, 2016

Related U.S. Application Data

(60) Provisional application No. 61/889,864, filed on Oct. 11, 2013.

(51) Int. Cl.
*C08G 59/14* (2006.01)
*C07C 217/08* (2006.01)
(Continued)

(52) U.S. Cl.
CPC ........ *C08G 59/1477* (2013.01); *C07C 217/08* (2013.01); *C07C 217/10* (2013.01); *C08L 63/00* (2013.01); *C08L 2205/025* (2013.01)

(58) Field of Classification Search
CPC .................................................. C08G 59/1477
See application file for complete search history.

(56) References Cited

U.S. PATENT DOCUMENTS

| 4,252,936 A | 2/1981 | Rinde et al. |
| 4,929,661 A * | 5/1990 | Noomen ................. C08K 5/17 |
| | | 524/259 |

(Continued)

OTHER PUBLICATIONS

Notification of Transmittal of the International Search Report and the Written Opinion of the International Searching Authority from corresponding PCT/US2014/060524 dated Mar. 19, 2015.

(Continued)

*Primary Examiner* — Megan McCulley
(74) *Attorney, Agent, or Firm* — Goodwin Procter LLP

(57) ABSTRACT

The present disclosure relates, in part, to an epoxy resin composition comprising: an epoxy resin; and an aliphatic polyamine (e.g., as a cross-linking agent), wherein the aliphatic polyamine comprises a compound having the structure of Formula (1): wherein each of R1 and R2 is independently selected from the group consisting of hydrogen, alkyl group, cycloalkyl group and aromatic group; or R1 and R2 together with the carbon atom to which they are attached form a cyclic ring; each of R3 and R4 is independently selected from the group consisting of hydrogen, alkyl group, cycloalkyl group and aromatic group.

(1)

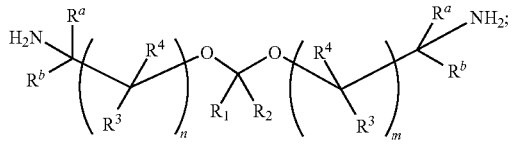

23 Claims, 2 Drawing Sheets

(51) Int. Cl.
C07C 217/10 (2006.01)
C08L 63/00 (2006.01)

(56) References Cited

U.S. PATENT DOCUMENTS

| | | | | |
|---|---|---|---|---|
| 9,080,004 | B2* | 7/2015 | Abrami | C08G 59/182 |
| 2002/0045057 | A1* | 4/2002 | Guritza | A61L 2/0082 |
| | | | | 428/540 |
| 2006/0014924 | A1* | 1/2006 | Hanley | C08G 59/24 |
| | | | | 528/407 |
| 2009/0030125 | A1 | 1/2009 | Vedage et al. | |
| 2009/0048370 | A1* | 2/2009 | Lutz | C08L 63/00 |
| | | | | 523/428 |
| 2009/0137777 | A1* | 5/2009 | Iwashima | C08G 59/12 |
| | | | | 528/503 |
| 2011/0048637 | A1* | 3/2011 | Kohli | C09J 163/00 |
| | | | | 156/307.1 |
| 2012/0301726 | A1 | 11/2012 | Staunton et al. | |
| 2013/0245204 | A1 | 9/2013 | Pastine et al. | |
| 2014/0221510 | A1* | 8/2014 | Liang | C08J 11/16 |
| | | | | 521/40 |
| 2016/0229949 | A1* | 8/2016 | Qin | C07C 317/32 |

OTHER PUBLICATIONS

PubChem. Compound Summary for CID 20541457. dated Dec. 5, 2007. [retrieved on Dec. 4, 2014]. Retrieved from the Internet. <URL: https://pubchem.ncbi.nlm.nih.gov/compound/20541457>. entire document.

* cited by examiner

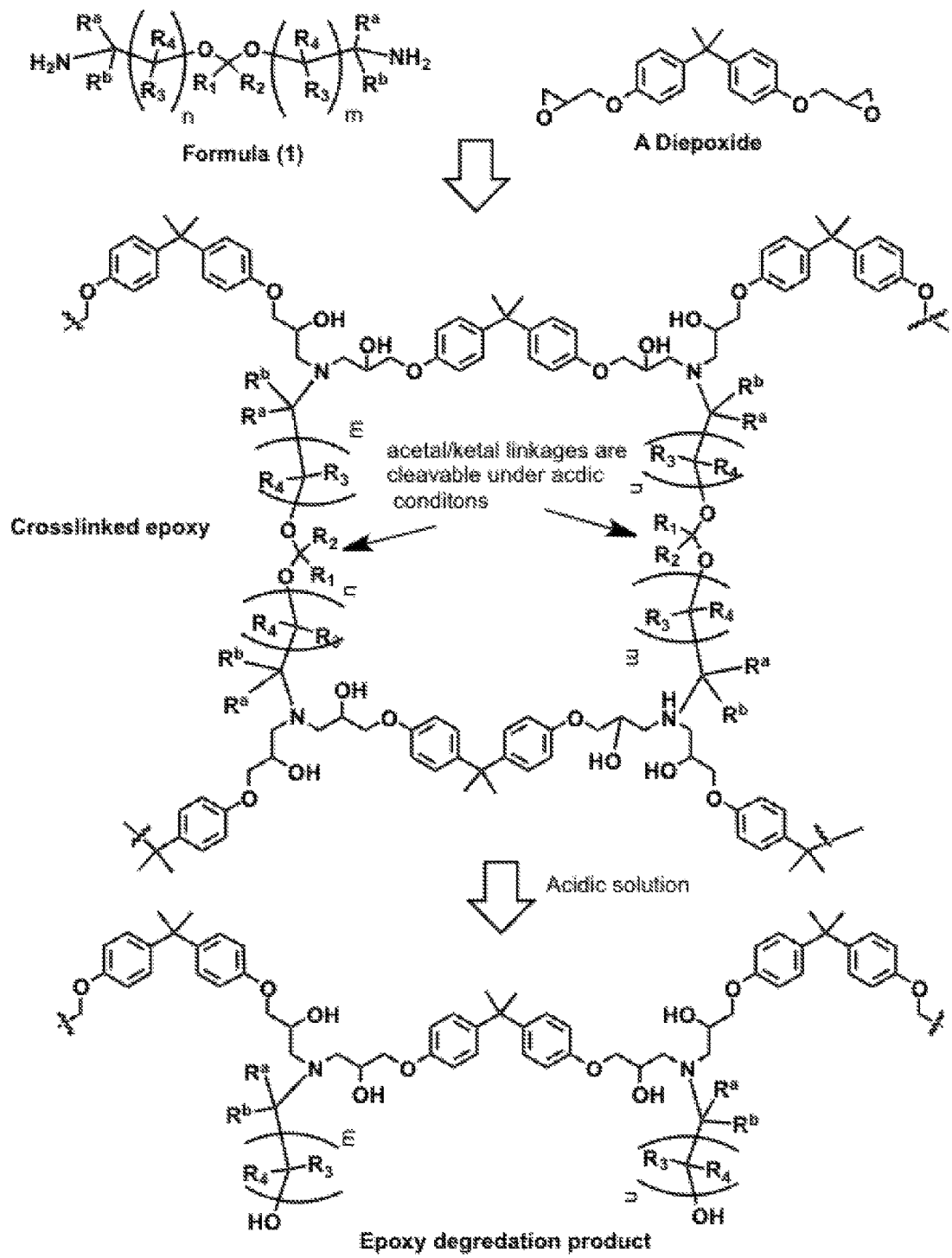
Figure 1. Generic cross-linked epoxy product and epoxy degradation product

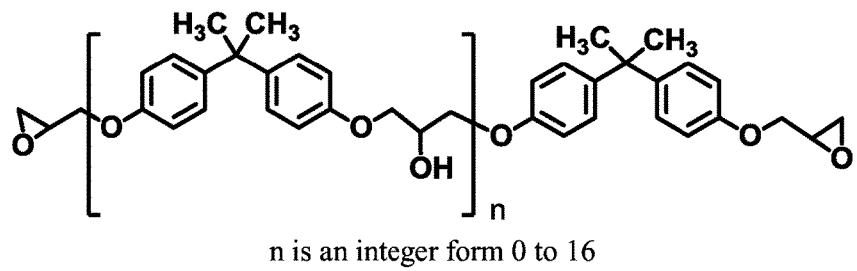
n is an integer form 0 to 16
DGEBPA or BPADGE
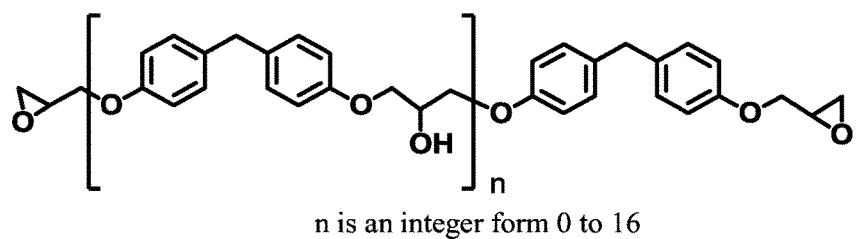
n is an integer form 0 to 16
DGEBPF or BPFDGE
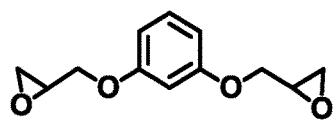
Diepoxide
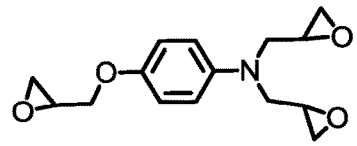
Triepoxide resin
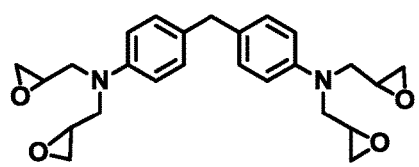
A tretra epoxide resin
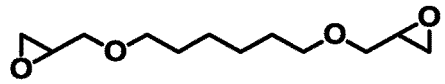
1,6-Hexanediol diglycidyl ether
Figure 2. Exemplary epoxy resins

STERICALLY HINDERED ALIPHATIC POLYAMINE CROSS-LINKING AGENTS, COMPOSITIONS CONTAINING THEM AND USES THEREOF

RELATED APPLICATIONS

The present application is a U.S. National Stage Application under 35 U.S.C. §371 of International Application No. PCT/US2014/060524, filed Oct. 14, 2014, titled STERICALLY HINDERED ALIPHATIC POLYAMINE CROSS-LINKING AGENTS, COMPOSITIONS CONTAINING THEM AND USES THEREOF, which claims priority under 35 U.S.C. §119(e) to U.S. provisional patent application U.S. Ser. No. 61/889,864, filed Oct. 11, 2013, the entire contents of which are incorporated herein by reference.

BACKGROUND

Described herein are epoxy resin compositions containing sterically hindered, reworkable aliphatic amines, e.g., that have long working times; and methods of their use.

BRIEF SUMMARY OF THE INVENTION

In one aspect, described herein is an epoxy resin composition comprising (i) an epoxy resin; and (ii) an aliphatic polyamine cross-linking agent comprising a compound having Formula (1):

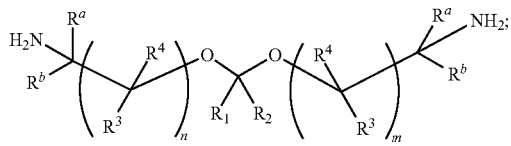

Formula (1)

wherein: each of $R^1$ and $R^2$ is independently selected from the group consisting of hydrogen, alkyl group, cycloalkyl group and aromatic group; or $R^1$ and $R^2$ together with the carbon atom to which they are attached form a cyclic ring; each of $R^3$ and $R^4$ is independently selected from the group consisting of hydrogen, alkyl group, cycloalkyl group and aromatic group; or $R^3$ and $R^4$ together with the carbon atom to which they are attached form a cyclic ring; each $R^a$ and $R^b$ is independently selected from the group consisting of alkyl group, cycloalkyl group and aromatic group; and each m and n is independently an integer ranging from 0 to 20.

In some embodiments, $R^1$ is alkyl (e.g., —$CH_3$). In some embodiments, $R^2$ is alkyl (e.g., —$CH_3$). In some embodiments, $R^1$ and $R^2$ are both alkyl (e.g., —$CH_3$).

In some embodiments, $R^1$ is hydrogen. In some embodiments, $R^2$ is hydrogen. In some embodiments, $R^1$ and $R^2$ are both hydrogen. In some embodiments, $R^1$ is hydrogen and $R^2$ is alkyl (e.g., —$CH_3$). In some embodiments, $R^1$ is alkyl (e.g., —$CH_3$) and $R^2$ is hydrogen.

In some embodiments, $R^3$ is hydrogen. In some embodiments, $R^4$ is hydrogen. In some embodiments, $R^3$ and $R^4$ are both hydrogen.

In some embodiments, $R^a$ is alkyl (e.g., —$CH_3$). In some embodiments, $R^b$ is alkyl (e.g., —$CH_3$). In some embodiments, $R^a$ and $R^b$ are both alkyl (e.g., —$CH_3$).

In some embodiments, m is 1.
In some embodiments, n is 1.
In some embodiments, the epoxy resin composition has working time of at least 5 hours (e.g., at least 5, 10, 12, 16, 20, 24, 32, 36, 48, 72 hours). In some embodiments, the epoxy resin composition has working time of at least 1, 2, 3, 4, 5, 6, or 7 days.

In some embodiments, the aliphatic polyamine is a sterically hindered aliphatic polyamine. In some embodiments, the sterically hindered aliphatic polyamine is of Formula (1-1):

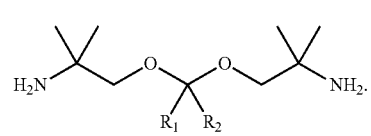

Formula (1-1)

In some embodiments, each of $R^1$ and $R^2$ is independently selected from the group consisting of hydrogen, alkyl group, cycloalkyl group and aromatic group. In some embodiments, $R^1$ and $R^2$ together with the carbon atom to which they are attached form a cyclic ring.

In some embodiments, $R^1$ is alkyl (e.g., —$CH_3$). In some embodiments, $R^2$ is alkyl (e.g., —$CH_3$). In some embodiments, $R^1$ and $R^2$ are both alkyl (e.g., —$CH_3$).

In some embodiments, $R^1$ is hydrogen. In some embodiments, $R^2$ is hydrogen. In some embodiments, $R^1$ and $R^2$ are both hydrogen. In some embodiments, $R^1$ is hydrogen and $R^2$ is alkyl (e.g., —$CH_3$). In some embodiments, $R^1$ is alkyl (e.g., —$CH_3$) and $R^2$ is hydrogen.

In some embodiments, the aliphatic polyamine is selected from the group consisting of:

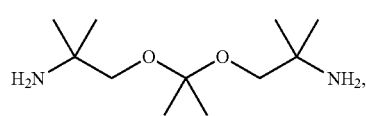

H-(1-1)

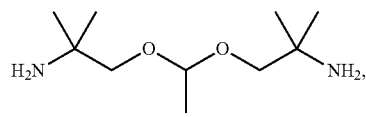

H-(1-2)

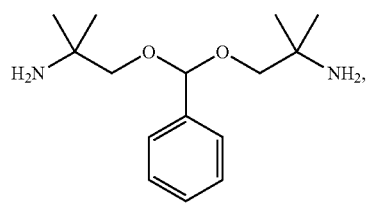

H-(1-3)

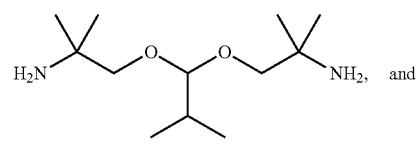

H-(1-4), and

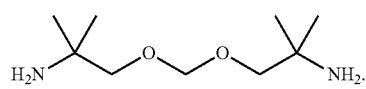

H-(1-5)

In some embodiments, the aliphatic polyamine is:

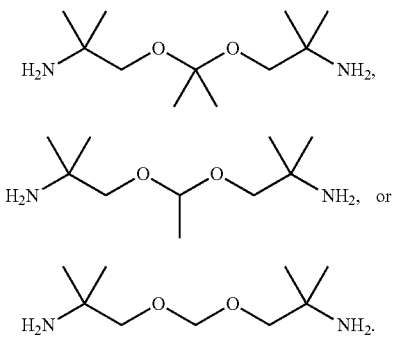

In some embodiments, an epoxy resin composition described herein includes an epoxy resin comprising an average of at least two epoxide groups per molecule (i.e. at least two epoxide groups per monomer of the epoxy resin). In some embodiments, an epoxy resin composition described herein includes an epoxy resin comprising a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin and combinations thereof. In some embodiments, an epoxy resin composition described herein includes an epoxy resin comprising a blend of a bisphenol-based epoxy resin having an epoxide equivalent weight (EEW) in the range of 160 to 220. In some embodiments, an epoxy resin composition described herein includes an epoxy resin comprising a bisphenol-based epoxy resin having an EEW in the range of 400 to 1500. In some embodiments, an epoxy resin composition described herein includes an epoxy resin comprising a blend of a first bisphenol-based epoxy resin having an epoxide equivalent weight (EEW) in the range of 160 to 220 and a second bisphenol-based epoxy resin having an EEW in the range of 400 to 1500. In some embodiments, an epoxy resin composition described herein includes an epoxy resin- or an epoxy resin blend having a viscosity in the range of about 100 cP to about 500,000 cP at room temperature. In some embodiments, an epoxy resin composition described herein includes an epoxy resin- or an epoxy resin blend having a viscosity in the range of about 1,000 cP to about 20,000 cP at room temperature. In some embodiments, an epoxy resin composition described herein includes an epoxy resin- or an epoxy resin blend having a viscosity in the range of about 8,000 cP to about 16,000 cP at room temperature. In some embodiments, the viscosity is at least 100 cP, 1,000 cP, 8,000 cP, 10,000 cP, 12,000 cP, 14,000 cP or 16,000 cP.

In some embodiments, an epoxy resin composition described herein further includes an auxiliary material. In one embodiment, an epoxy resin composition described herein further includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, gloss additive, flame retardant, and combinations thereof.

In some embodiments, an epoxy resin composition described herein comprises an additional amino molecule (e.g., an additional amine, e.g., aliphatic polyamine, e.g., aliphatic polyamine that does not have a cleavable linking group (e.g., acetal group, ketal group). In some embodiments, the amino molecule comprises >2 N—H hydrogens.

In some embodiments, an epoxy resin composition described herein further comprises an amino molecule containing ≤2 N—H hydrogens.

In some embodiments, an epoxy resin composition described herein comprises an epoxy resin, further comprising an amino molecule containing ≤2 N—H hydrogens. In one embodiment, the amino molecule comprising ≤2 N—H hydrogens, is selected from the group consisting of a primary monoamine compound and a bis(secondary) diamine compound. In one embodiment, the amino molecule containing ≤2 N—H hydrogens, is selected from the group comprising monoethanolamine, diethanolamine, 3-aminopropanol, 2-aminopropanol, aminobenzylamine, aniline, p-anisidine, butylamine, piperazine, and N,N'-dimethylethylenediamine, tert-butylamine, sec-butylamine and combinations thereof. In one embodiment, the amino molecule containing ≤2 N—H hydrogens is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. % of the epoxy resin composition.

In some embodiments, an epoxy resin composition described herein further includes a reinforcing agent. For example, the epoxy resin composition can be layered with a reinforcing agent. In one embodiment, the reinforcing agent comprises at least one reinforcing component selected from the group comprising glass fibers, aramid fibers, graphite fibers, carbon fibers, natural fibers, and non-natural fibers.

In some embodiments, an epoxy resin composition described herein has a glass transition temperature (Tg) of about 60° C. to about 155° C. (e.g., about 70 to about 155° C., about 80 to about 155° C., about 90 to about 155° C., about 100 to about 155° C.); about 60° C. to about 135° C. (e.g., about 70 to about 135° C., about 80 to about 135° C., about 90 to about 135° C., about 100 to about 135° C.); 60 to about 115° C. (e.g., about 70 to about 115° C., about 80 to about 115° C., about 90 to about 115° C., about 100 to about 115° C.). In some embodiments, an epoxy resin composition described herein has a glass transition temperature (Tg) of about 100° C. to about 120° C.

In some embodiments, an epoxy resin composition described herein has a glass transition temperature (Tg) of at least 60° C. (e.g., at least 70° C., 80° C., 90° C., or 100° C.).

In some embodiments, an epoxy resin composition described herein has a tensile strength of about 7,000 to about 13,000 psi (e.g., about 8,000 to about 12,000 psi, about 9,000 to about 11,000 psi).

In some embodiments, an epoxy resin composition described herein has a tensile strength of at least 7,000 psi (e.g., at least 8,000 psi, 9,000 psi, 10,000 psi).

In some embodiments, an epoxy resin composition described herein has an elongation at break of about 2 to about 10% (e.g., about 3 to about 9%).

In some embodiments, an epoxy resin composition described herein has an elongation at break of at least 2% (e.g., at least 2%, 3%, 4%, 5%).

In some embodiments, an epoxy resin composition described herein has a flexural strength of about 12,000 to about 21,000 psi (e.g., about 12,000 to about 18,000 psi, about 13,000 to about 17,000 psi).

In some embodiments, an epoxy resin composition described herein has a flexural strength of at least 12,000 psi (e.g., at least 13,000 psi, 14,000 psi, or 15,000 psi).

In some embodiments, an epoxy resin composition described herein has a flexural modulus of about 300,000 to about 600,000 psi (e.g., about 300,000 to about 500,000 psi).

In some embodiments, an epoxy resin composition described herein has a flexural modulus of at least 300,000 psi (e.g., at least 350,000 psi, 400,000 psi, 450,000 psi).

In one aspect, described herein is a method of curing an epoxy resin composition, comprising (i) providing an epoxy resin composition (e.g., an epoxy resin composition described herein, e.g., an epoxy resin composition of Formula (1), and (ii) heating the epoxy resin composition.

In some embodiments, the epoxy resin composition is heated to a temperature range of about 20° C. to about 250° C. (e.g., about 20° C. to about 180° C., about 20° C. to about 120° C.).

In some embodiments, the epoxy resin composition is heated to at least about 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C.

In some embodiments, the epoxy resin composition has a working time of about 5, 8, 12, 15, 18, 24, 30, 36, 40, 48, 60, or 72 hours or more (e.g., at room or ambient temperature).

In some embodiments, the epoxy resin composition has an out-life of about 1 week to about 1 year. In some embodiments, the epoxy resin composition has an out-life of at least 1, 2, 3, or 4 weeks; at least 1, 2, 3, 4, 5, 6, 7, 8, 9, 10, 11, or 12 months; at least 1 year.

In another aspect, described herein is a method of curing an epoxy resin composition. In one embodiment, the method of curing the epoxy resin composition comprises (i) providing an epoxy resin composition described herein; and (ii) curing the epoxy resin composition by exposing it to an energy from an energy source, thereby causing the epoxy resin composition to form a cross-linked polymer matrix. In one embodiment, the curing step comprises irradiating the epoxy resin composition with a curing energy. In one embodiment, the curing step comprises irradiating the epoxy resin composition with an electromagnetic radiation. In one embodiment, the curing step comprises irradiating the epoxy resin composition with an ultraviolet ("UV") light energy. In one embodiment, the curing step comprises curing the epoxy resin composition by the application of an induction heat energy source thereto.

In some embodiments, an epoxy resin composition described herein can be cured with any suitable energy source. In some embodiments, the energy source is an electromagnetic energy source. In some embodiments, the energy source is an electromagnetic energy source selected from the group consisting of carbon dioxide lasers, Nd:YAG lasers Ho:YAG lasers, Er:YAG lasers, diode lasers and ruby lasers.

In some embodiments, an epoxy resin composition described herein can be cured by heating the epoxy resin composition.

In another aspect, described herein is a cross-linked polymer matrix derived from an epoxy resin and a cross-linking group derived from an aliphatic polyamine cross-linking agent comprising a compound represented by Formula (1):

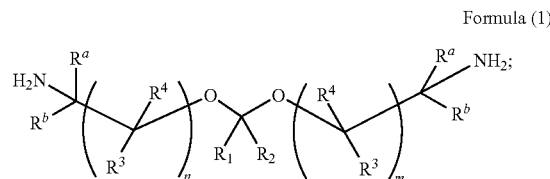

Formula (1)

wherein: each of $R^1$ and $R^2$ is independently selected from the group consisting of hydrogen, alkyl group, cycloalkyl group and aromatic group; or $R^1$ and $R^2$ together with the carbon atom to which they are attached form a cyclic ring; each of $R^3$ and $R^4$ is independently selected from the group consisting of hydrogen, alkyl group, cycloalkyl group and aromatic group; or $R^3$ and $R^4$ together with the carbon atom to which they are attached form a cyclic ring; each $R^a$ and $R^b$ is independently selected from the group comprising alkyl group, cycloalkyl group and aromatic group; and each m and n is independently an integer ranging from 0 to 20. In some embodiments, the cross-linked polymer matrix has cross-links derived from the aliphatic polyamine cross-linking agent.

In some embodiments, a cross-linked polymer matrix described herein comprises diepoxide monomers. In some embodiments, a cross-linked polymer matrix described herein is derived from a diepoxide resin. In some embodiments, a cross-linked polymer matrix described herein comprises a cross-linked epoxy resin derived from an epoxy resin selected from a group consisting of glycidyl ether epoxy resin, glycidyl amine epoxy resin, alicyclic epoxy resin, aliphatic epoxy resin, phenolic epoxy resin, and combinations thereof. In some embodiments, a cross-linked polymer matrix described herein further includes a reinforcement material. In some embodiments, a cross-linked polymer matrix described herein further includes a reinforcement material selected from a fibrous material or a non-fibrous material.

In some embodiments, the fibrous material is selected from a group consisting of glass fiber, carbon fiber, natural fiber, and chemical fiber. In some embodiments, the non-fibrous material is selected from a group consisting of carbon nanotube, carbon black, metal nanoparticle, organic nanoparticle, iron oxide, boron nitride, and combinations thereof.

In some embodiments, a cross-linked polymer matrix described herein further includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive, flame retardant, and combinations thereof.

In another aspect, described herein is a reinforced composite material comprising a cross-linked polymer matrix described herein. In some embodiments, a reinforced composite material described herein is prepared by at least one method selected from a group consisting of wet lay-up, vacuum infusion, infusion, filament winding, and resin transfer molding, prepreg, compression molding, pultrusion and wet pressing.

In another aspect, described herein is a method for recycling a cross-linked polymer matrix or a reinforced composite material described herein. In some embodiments, a method for recycling a cross-linked polymer matrix or a reinforced composite material described herein comprises degrading the cross-linked polymer matrix or the reinforced composite material using an acid in the presence of a solvent (e.g., methanol, ethanol, ethylene glycol, isopropyl alcohol, butyl alcohol, pentanol, hexanol, heptanol, octanol alcohol, nonyl alcohol, water). In some embodiments, degrading the cross-linked polymer matrix occurs through the acid hydrolysis of an acetal or ketal group. In some embodiments, a method for recycling a cross-linked polymer matrix or a reinforced composite material described herein comprises degrading the cross-linked polymer matrix or the reinforced composite material under a heating condition.

In some embodiments, a method for recycling a cross-linked polymer matrix or a reinforced composite material described herein comprises degrading the cross-linked polymer matrix or the reinforced composite material by exposing the cross-linked polymer matrix or the reinforced composite material to an acid selected from the group consisting of hydrochloric acid, acetic acid, lactic acid, formic acid, propionic acid, citric acid, methane sulfonic acid, p-toluene sulfonic acid, sulfuric acid, benzoic acid, phthalic acid, and combinations thereof.

In some embodiments, the solvent is selected from the group consisting of methanol, ethanol, ethylene glycol, isopropyl alcohol, butyl alcohol, pentanol, hexanol, heptanol, octanol alcohol, nonyl alcohol, water, and combinations thereof.

In some embodiments, the acid has a concentration in a solvent in a range of from about 2% to about 90% by weight. In some embodiments, the acid has a concentration in a solvent in a range of from about 5% to about 25% by weight.

In some embodiments, a method for recycling a cross-linked polymer matrix or a reinforced composite material described herein comprises degrading the cross-linked polymer matrix or the reinforced composite material at a temperature ranging from about 15° C. to about 400° C.

In some embodiments, a method for recycling a cross-linked polymer matrix or a reinforced composite material described herein comprises degrading the cross-linked polymer matrix or the reinforced composite material at a temperature ranging from about 60° C. to about 120° C. (e.g., about 80° C. to about 120° C.).

In some embodiments, a method for recycling a cross-linked polymer matrix or a reinforced composite material described herein comprises degrading the cross-linked polymer matrix or the reinforced composite material comprises heating the cross-linked polymer matrix or the reinforced composite material for a time ranging from about 1 hour to about 48 hours. In some embodiments, a method for recycling a cross-linked polymer matrix or a reinforced composite material described herein comprises degrading the cross-linked polymer matrix or the reinforced composite material comprises heating the cross-linked polymer matrix or the reinforced composite material for a time ranging from about 1 hour to about 24 hours. In some embodiments, a method for recycling a cross-linked polymer matrix or a reinforced composite material described herein comprises degrading the cross-linked polymer matrix or the reinforced composite material comprises heating the cross-linked polymer matrix or the reinforced composite material for a time ranging from about 1 hour to about 12 hours.

In some embodiments, a method for recycling a cross-linked polymer matrix or a reinforced composite material described herein further comprises a step of recovering a degradation product of the cross-linked polymer matrix or of the reinforced composite material via a precipitation process or a filtration process. In some embodiments, a method for recycling a cross-linked polymer matrix or a reinforced composite material described herein further comprises a step of recovering a degradation product of the cross-linked polymer matrix or of the reinforced composite material via a precipitation process and a filtration process.

In another aspect, described herein is a degradation product resulting from a method for recycling a cross-linked polymer matrix or a reinforced composite material described herein. In some embodiments, described herein is a degradation product resulting from a method for recycling a cross-linked polymer matrix and a reinforced composite material described herein.

In another aspect, described herein is an adhesive composition comprising the epoxy composition described herein.

In another aspect, described herein is a method of removing, recovering, or recycling an adhesive composition described herein, e.g., wherein the method comprises degrading the adhesive composition using an acid in the presence of a solvent.

In another aspect, described herein is a method of removing, recovering, or recycling an adhesive composition described herein, wherein the method comprises degrading the adhesive composition using an acid in the presence of a solvent.

In another aspect, described herein is a coating composition comprising an epoxy composition described herein.

In another aspect, described herein is a method of removing, recovering, or recycling of an epoxy coating composition described herein, e.g., comprising degrading the epoxy coating using an acid in the presence of a solvent.

In another aspect, described herein is an encapsulating material comprising an epoxy composition described herein.

In another aspect, described herein is a method of removing, recovering, or recycling of an epoxy encapsulation material described herein, the method comprising degrading the epoxy encapsulation material using an acid in the presence of a solvent.

In some embodiments of an epoxy resin composition described herein, the polyamine, e.g., comprising the compound of Formula (1), has a working time of from about 5 hours to about 48 hours (e.g., about 12 hours to about 48 hours, about 24 hours to about 48 hours) or more, e.g., prior to the aliphatic polyamine cross-linking transforming the epoxy resin composition to a partially or a fully cross-linked polymer matrix.

In some embodiments of an epoxy resin composition described herein, after application of an initiating energy to the epoxy resin composition, the epoxy resin composition has a working time of from about 48 hours to about 5 hours (e.g., about 48, 36, 32, 28, 24, 18, 12, 5 hours) or less, e.g., e.g., prior to the epoxy resin composition forming a partially or a fully cross-linked polymer matrix.

In some embodiments of an epoxy resin composition described herein, the epoxy resin composition has a working time of from about 5 hours to about 48 hours (e.g., about 12 hours to about 48 hours, about 24 hours to about 48 hours) or more at room temperature, e.g., prior to transforming to a partially or a fully cross-linked polymer matrix.

In some embodiments, the aliphatic polyamine cross-linking agent comprising the compound of Formula (1) is present in an amount sufficient to impart to the epoxy resin composition a setting time period no less than about 48 hours.

In some embodiments, the epoxy resin composition has a working time sufficient to allow manipulation of the epoxy resin composition, e.g., before energy is applied to it to form a cross-linked polymer matrix.

In some embodiments, the working time temperature is from 60 to 180° C.

In another aspect, described herein is a method of altering the working time of a curable epoxy resin composition to compensate for ambient temperatures comprising: forming a stable resin blend including a cross-linkable epoxy resin; selecting a cross-linking agent for the epoxy resin from the group consisting of a polyamine cross-linking agent comprising a compound having Formula (1):

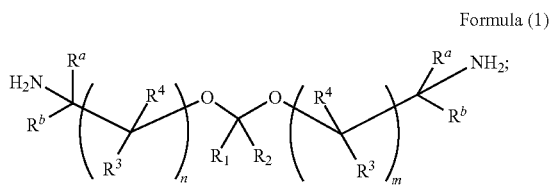

Formula (1)

wherein: each of $R^1$ and $R^2$ is independently selected from the group consisting of hydrogen, alkyl group, cycloalkyl group and aromatic group; or $R^1$ and $R^2$ together with the carbon atom to which they are attached form a cycloalkyl group; each of $R^3$ and $R^4$ is independently selected from the group consisting of hydrogen, alkyl group, cycloalkyl group and aromatic group; or $R^3$ and $R^4$ together with the carbon atom to which they are attached form a cyclic ring; each $R^a$ and $R^b$ is independently selected from the group consisting of alkyl group, cycloalkyl group and aromatic group; and each m and n is independently an integer ranging from 0 to 20; and wherein the selection is made such that a mixture of the cross-linking agent and the epoxy resin has a long working time at or near ambient temperatures.

In some embodiments, the curable epoxy resin composition exhibits a working time of at least 6 hours. In some embodiments, the curable epoxy resin composition exhibits a working time of at least 12 hours. In some embodiments, the curable epoxy resin composition exhibits a working time of at least 24 hours. In some embodiments, the curable epoxy resin composition exhibits a working time of at least 36 hours. In some embodiments, the curable epoxy resin composition exhibits a working time of at least 48 hours after contacting the cross-linking agent. In some embodiments, the curable epoxy resin composition exhibits a working time ranging from about 12 hours to about 72 hours. In some embodiments, the curable epoxy resin composition exhibits a working time ranging from about 24 hours to about 72 hours. In some embodiments, the curable epoxy resin composition exhibits a working time ranging from about 48 hours to about 72 hours. In some embodiments, the curable epoxy resin composition exhibits a working time ranging from about 2 days to about 1 week. In some embodiments, the curable epoxy resin composition exhibits a working time ranging from about 1 week to about 1 month. In some embodiments, the curable epoxy resin composition exhibits a working time ranging from about 1 month to about 3 months. In some embodiments, the curable epoxy resin composition exhibits a working time ranging from about 3 months to about 6 months. In some embodiments, the curable epoxy resin composition exhibits a working time of at least 5, 6, 7, 8, 10, 12, 15, 18, 20, or 24 hours; at least 1, 2, 3, 4, 5, 6, or 7 days; at least 1, 2, 3, or 4 weeks; at least 1, 2, 3, 4, 5, 6, 7, or 8 months.

In another aspect, described herein is a polyamine (e.g., amine hardener) compound of the Formula (1):

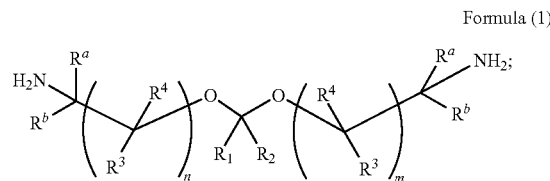

Formula (1)

wherein: each of $R^1$ and $R^2$ is independently selected from the group consisting of hydrogen, alkyl group, cycloalkyl group and aromatic group; or $R^1$ and $R^2$ together with the carbon atom to which they are attached form a cyclic ring; each of $R^3$ and $R^4$ is independently selected from the group consisting of hydrogen, alkyl group, cycloalkyl group and aromatic group; or $R^3$ and $R^4$ together with the carbon atom to which they are attached form a cyclic ring; each $R^a$ and $R^b$ is independently selected from the group consisting of alkyl group, cycloalkyl group and aromatic group; and each m and n is independently an integer ranging from 0 to 20.

In some embodiments, $R^1$ is alkyl (e.g., —$CH_3$). In some embodiments, $R^2$ is s alkyl (e.g., —$CH_3$). In some embodiments, $R^1$ and $R^2$ are both alkyl (e.g., —$CH_3$).

In some embodiments, $R^1$ is hydrogen. In some embodiments, $R^2$ is hydrogen. In some embodiments, $R^1$ and $R^2$ are both hydrogen. In some embodiments, $R^1$ is hydrogen and $R^2$ is alkyl (e.g., —$CH_3$). In some embodiments, $R^1$ is alkyl (e.g., —$CH_3$) and $R^2$ is hydrogen.

In some embodiments, m is 1.

In some embodiments, n is 1.

In some embodiments, $R^3$ is hydrogen. In some embodiments, $R^4$ is hydrogen. In some embodiments, $R^3$ and $R^4$ are both hydrogen.

In some embodiments, $R^a$ is alkyl (e.g., —$CH_3$). In some embodiments, $R^b$ is alkyl (e.g., —$CH_3$). In some embodiments, $R^a$ and $R^b$ are both alkyl (e.g., —$CH_3$).

In another aspect, described herein is a polyamine (e.g., amine hardener) compound of the Formula (1-1):

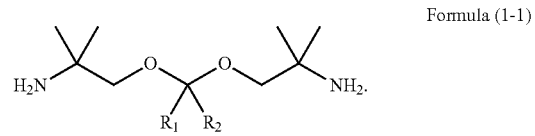

Formula (1-1)

In some embodiments, each of $R^1$ and $R^2$ is independently selected from the group consisting of hydrogen, alkyl group, cycloalkyl group and aromatic group. In some embodiments, $R^1$ and $R^2$ together with the carbon atom to which they are attached form a cycloalkyl group.

In some embodiments, $R^1$ is alkyl (e.g., —$CH_3$). In some embodiments, $R^2$ is alkyl (e.g., —$CH_3$). In some embodiments, $R^1$ and $R^2$ are both alkyl (e.g., —$CH_3$).

In some embodiments, $R^1$ is hydrogen. In some embodiments, $R^2$ is hydrogen. In some embodiments, $R^1$ and $R^2$ are both hydrogen. In some embodiments, $R^1$ is hydrogen and $R^2$ is alkyl (e.g., —$CH_3$). In some embodiments, $R^1$ is alkyl (e.g., —$CH_3$) and $R^2$ is hydrogen.

In some embodiments, the polyamine is selected from the group consisting of:

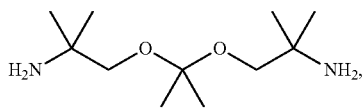
H-(1-1)

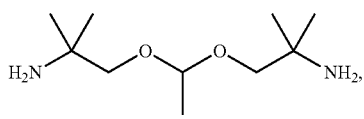
H-(1-2)

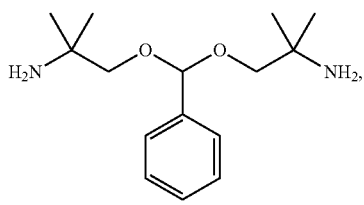
H-(1-3)

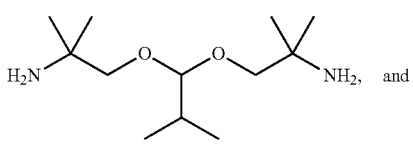
H-(1-4)
and

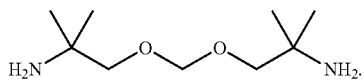
H-(1-5)

In some embodiments, the polyamine is:

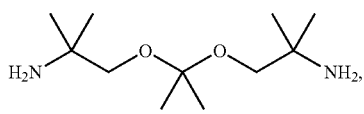
H-(1-1)

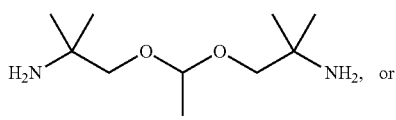
H-(1-2)
or

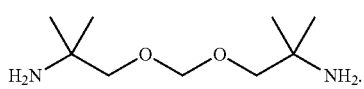
H-(1-5)

In another aspect, described herein is a method for recycling a reinforced composite described herein. In one embodiment, the method for recycling the reinforced composite comprises a step of degrading the cross-linked polymer matrix using an acid. In one embodiment, the degradation of the cross-linked polymer matrix is carried out (i.e., performed) using an acid in the presence of a solvent. In one embodiment, the degradation of the cross-linked polymer matrix is carried out (i.e., performed) using an acid under a heating condition.

In another aspect, described herein is a degradation product resulting from the method for recycling a reinforced composite described herein.

In another aspect, described herein is the use of any of the epoxy compositions described herein as an adhesive, a coating material, or an encapsulating material; wherein the epoxy composition can be removed, recycled, or dissolved from the article in contact with said epoxy composition via a method of degrading the epoxy composition described herein.

In another aspect, described herein is the use of any of the epoxy compositions described herein as an adhesive, a coating material, or an encapsulating material; wherein the epoxy composition is not removed, recycled, or dissolved from the article in contact with said epoxy composition.

BRIEF DESCRIPTION OF THE DRAWINGS

FIG. 1 depicts a generic cross-linked epoxy product and a generic epoxy degradation product; and FIG. 2 depicts exemplary epoxy resins that can be used in accordance with exemplary embodiments described herein.

DETAILED DESCRIPTION

The present subject matter will now be described more fully hereinafter with reference to the accompanying Figures, Tables, and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

Epoxy or epoxy compositions generally refers to the cured end product of epoxy resins. Epoxy curing involves at least two phenomena, polymerization and cross-linking. Each phenomenon is complex, and the two are often in competition during the overall curing process. Curing may be achieved by reacting epoxy with itself (e.g., homopolymerization) or with curing agents, e.g., curatives or hardeners (e.g., aliphatic polyamines, e.g., aliphatic polyamines of the Formula (1)). During the initial stage of curing, polymerization is typically favored as a result of the reactivity of curing agents (i.e., the reactive functional groups present in the curing agents). For example, where a curing agent has terminal primary amines or secondary amine groups, reactions of the primary amine groups with epoxy groups of epoxy resin will be favored over reactions of the secondary amine groups (e.g., with epoxy groups). Therefore, generally polymerization of curing agents and epoxy resins precedes cross-linking reactions between them (e.g., reactions with the secondary amine groups). Such a polymerization reaction typically involves an addition reaction between an epoxide and an amine group, and thus would tend to follow a rate equation for addition polymerization. The molecular weight of the growing polymer increases (e.g., until the molecular weight approaches infinity), so that almost all monomers are connected by at least one bond and a polymeric network is formed. At this point, sometimes called the "gel point", the polymer possesses high molecular weight and few cross-links, and thus behaves much like a very high molecular weight thermoplastic (e.g., a plastic that is pliable or moldable above a specific temperature and returns to the solid state on cooling).

The second stage of the curing process, cross-linking, becomes the dominant phenomenon once the gel point is reached due to the lack of free monomers (i.e., monomer of the curing agent(s)). The cross-linking reaction involves interchain bonding of intrachain reactive sites, between either intrachain epoxides or secondary amine sites. Although cross-linking is a different phenomenon than polymerization, the rate of chemical conversion of the epoxide groups is unaffected (e.g., is similar or unchanged relative to the polymerization rate) in most epoxy systems. The cross-linking reactions produce a growing network and reduce the mobility of the chain segments. The growth of the network results in mechanical and thermal stabilization of the structure, resulting in increasing modulus and glass transition (Tg).

At a certain high degree of cross-linking, the increasing molecular weight of the structure exceeds the molecular weight which is thermodynamically stable as a rubber, and the material transforms into a glass, a process referred to as vitrification. In a glassy state, the mobility of reactants is severely restricted, reducing the rate of the reaction to a diffusion-controlled reaction, which is much slower. Further conversion is still possible, however, the rate is much slower since the process relies on diffusion rather than mobility to bring the reactants together. When the cross-linking reaction exhausts all the reactive sites available, the resulting structure is hard (i.e., has a high modulus) and insoluble due to a high degree of interchain bonding.

Since chemicals react in definite proportions, theoretically, a given weight of an epoxy resin will react with a given "equivalent," or "stoichiometric," amount of polyamine curing agent to form a polymeric product if the conditions are such that the reaction can proceed to completion. Therefore in general, with epoxies or epoxy resins, when the curing agent contains primary amine groups, as is the case with some embodiments of the aliphatic polyamine cross-linking agent described herein, the first step of the two stage curing process discussed above involves the oxirane ring in the epoxy resin undergoing a ring opening reaction with an amine group of the aliphatic polyamine cross-linking agent to produce an aminoalcohol product. In the second step of the two stage curing process the aminoalcohol product, a reacted amine nitrogen (i.e., as a "secondary" amine group), can react with yet another epoxy (i.e., oxirane ring) to form a higher molecular weight or branched polymer (e.g., to form a higher molecular weight and branched polymer). Thus, most or all of the —NH$_2$, or the primary amine groups of the aliphatic polyamine cross-linking agent, will require two oxirane groups for complete reaction.

When the reactants are, for example, polyamine curing agent H-(1-1), described herein below, and a typical bisphenol A-type epoxy resin, such as BPADGE, each molecule of polyamine curing agent H-(1-1), with its two primary amine groups, may react with four oxirane groups as shown in Scheme A below. Notably, epoxy resins such as BPADGE can, e.g., polymerize by homopolymerization and therefore not be present in the monomeric form depicted.

Scheme A

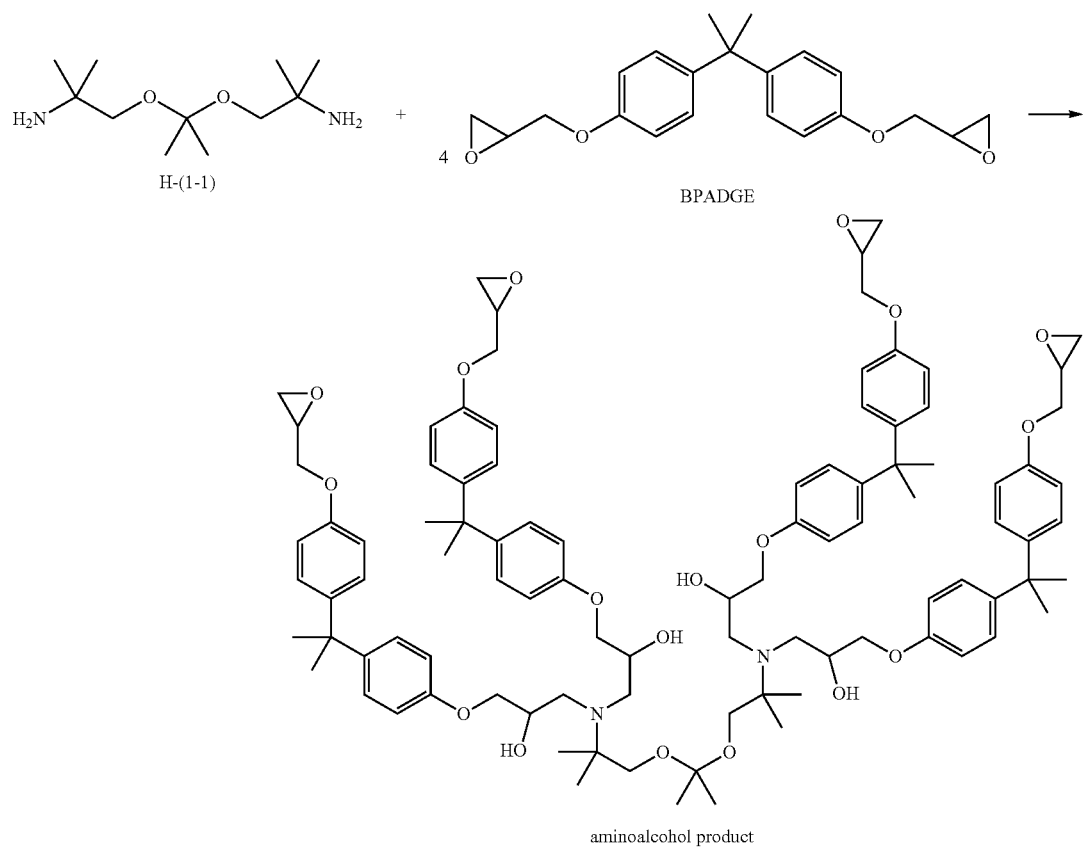

aminoalcohol product

Therefore, in regard to chemical balancing, the optimum, proportions of reactants relative to epoxy systems can be obtained at least in of two ways: (1) by calculating the quantities involved from the chemical "equivalent" weights of all the reactants, or (2) by determining the balance empirically. Generally, epoxy resin's epoxide equivalent weight (EEW) is defined by the following equation 1 (eq.1):

$$\text{Epoxy resin epoxide } eq. \text{ wt. (or } EEW) = \frac{(\text{MW of epoxy resin})}{(\text{no. of epoxides in the epoxy resin})} \quad (\text{eq. 1})$$

wherein MW of epoxy resin represents molecular weight of the epoxy resin.

In some embodiments, an epoxy resin composition described herein includes an epoxy resin comprising a blend of a bisphenol-based epoxy resin having an epoxide equivalent weight (EEW) in the range of 160 to 220. In some embodiments, an epoxy resin composition described herein includes an epoxy resin comprising a bisphenol-based epoxy resin having an EEW in the range of 400 to 1500. In some embodiments, an epoxy resin composition described herein includes an epoxy resin comprising a blend of a first bisphenol-based epoxy resin having an epoxide equivalent weight (EEW) in the range of 160 to 220 and a second bisphenol-based epoxy resin having an EEW in the range of 400 to 1500.

Analogously, amine hydrogen equivalent weight is defined by the following equation 2 (eq.2):

$$\text{Amine hydrogen } eq. \text{ wt. (or } AEW) = \frac{(\text{MW of amine})}{(\text{no. of active hydrogens})} \quad (\text{eq. 2})$$

wherein MW of amine represents molecular weight of the amine.

The stoichiometric ratio of an amine hardener to use with epoxy resin having a known or calculable epoxide equivalent weight EEW can be calculated using the following equation 3 (eq.3):

$$\text{stoichiometric ratio of amine} = \frac{(\text{Amine } H \; eq. \text{ wt} \times 100)}{(\text{Epoxide } eq. \text{ wt. of resin})} \quad (\text{eq. 3})$$

As an example, EEW of bisphenol A diglycidyl ether (BPADGE), AEW of H-(1-1), and stoichiometric ratio of H-(1-1) are calculated as follows.

H-(1-1) has a molecular weight of 218.34 atomic mass units (amu) and four active hydrogens. According to eq. 2, AEW of H-(1-1) equals 54.585 (or 218.34÷4). BPADGE has a molecular weight of 340.41 amu and two epoxides. According to eq.1, EEW of BPADGE equals 170.205 (or 340.41÷2). According to eq.3, the stoichiometric ratio of H-(1-1) to use with BPADGE equals 32.07 (or [54.585×100]÷170.205). In other words, if one wishes to use a stoichiometric amount of H-(1-1) with BPADGE, one would need 32.07 parts H-(1-1) by wt. per 100 parts resin (BPADGE) or 32.07 g of H-(1-1) for every 100 g of BPADGE used.

Generally, the empirical (i.e., experimental) method of chemical balancing is preferred, e.g., at least because actual working conditions are used. However, in some embodiments, calculating the quantities involved from the chemical "equivalent" weights of all the reactants is used. Differences in the two calculating methods may arise from factors such as steric hindrance or catalytic effects. However, such differences may be easily corrected empirically through adjustments to the experimental conditions.

In one aspect, described herein is a method of using certain sterically hindered aliphatic polyamines as curing agents for epoxy resins. In some embodiments, epoxy resin compositions including the sterically hindered polyamines described herein exhibit long working times. Accordingly, in some embodiments, epoxy resin compositions described herein are useful in epoxy applications that require long working times. Examples of such epoxy applications include, but are not limited to, epoxy composites made via filament winding processes, epoxy composites made via filament winding type processes, epoxy composites made via pultrusion-type processes, epoxy composites made via prepreg-type processes, latent adhesive formulations, epoxy molding compounds and epoxy powder coatings. In some embodiments, the sterically hindered aliphatic polyamines described herein include one or more cleavable links (e.g., an acetal or ketal group). Cleavable links such as an acetal or ketal group described herein can provide ability to rework epoxy compositions. In some embodiments, the sterically hindered aliphatic polyamines described herein are suitable for use in reworkable epoxy compositions.

As discussed above, epoxy resin curing involves polymerization and cross-linking. Generally the polymerization of curing agents and epoxy resins precedes cross-linking reactions between them. During the polymerization step, the molecular weight of the growing polymer increases, so that almost all monomers are connected by at least one bond and a polymeric network is formed. The duration of time between initial mixing of the epoxy resin and the curing agent, and the mixture curing to an amorphous solid state is sometimes called the "gel time". The gel time of an epoxy composition at a given temperature is an essential parameter for applications that require the liquid state because after the mixed system hardens it is no longer pourable or otherwise useable. Unlike the sterically hindered polyamine (e.g., a sterically hindered polyamine of Formula (1), conventional polyamines used in the art (e.g. an aliphatic polyamine that is not sterically hindered), hardens usually near the point at which cross-linking occurs (i.e., the time for an epoxy composition comprising a conventional polyamine (e.g., an aliphatic polyamine that is not sterically hindered).

As described herein, "working time" refers to the time it takes to for a 100 gram mass (or greater than a 100 gram mass) of epoxy resin composition to reach a solidified state at room temperature, wherein "room temperature" is defined by the temperature range of 22-27° C. "Gel-time," as described herein, is used interchangeably with "working time". Once the epoxy composition described herein reaches an amorphous solid state at room temperature, the epoxy composition is referred to as being in a "B-stage" state (i.e., it is not cross-linked).

The working time of a epoxy resin composition begins when a hardener (e.g., an aliphatic polyamine cross-linking agent, e.g., an aliphatic polyamine cross-linking agent of the Formula (1)) and an epoxy resin (e.g., BPADGE) are added together or are first present together in the polymer composition. In some embodiments, the working time of the epoxy resin composition begins when polymerization of the curing agents and epoxy resins begins. In some embodiments, the working time for the epoxy resin composition described herein is at least 5 hours (e.g., 5, 10, 12, 16, 18, 20, 24, 30, 48, 60, or 72 hours). In some embodiments, the working time for the epoxy resin composition described herein is longer in duration (e.g., 1, 2, 3, 4, 5, 6, 7, 8, 9, 10, 11, 12, 13, 14, 15 or more times longer in duration) than the working time for an epoxy resin composition comprising a conventional hardener (e.g., an aliphatic polyamine, e.g., an aliphatic polyamine that is not sterically hindered). Working time also refers to the duration of time for which a composition (e.g., a composition as described herein, e.g., a composition comprising an epoxy resin and an aliphatic polyamine cross-linking agent (e.g., an aliphatic polyamine cross-linking agent of Formula (1)) retains a viscosity in which the composition can be e.g., easily poured, or can be used e.g., to impregnate a fiber such as, fiber glass or carbon fiber. In some embodiments, the working time is the time for which a composition (e.g., a composition as described herein, e.g., a composition comprising an epoxy resin and an aliphatic polyamine cross-linking agent (e.g., an aliphatic polyamine cross-linking agent of Formula (1)) retains a viscosity of less than 10,000 cP. For filament winding, for example, a working time of at least 10 hours, and preferably greater than 1 day is desired. Epoxy resin composition manufacturing or processing described herein exhibit long working time or long pot-life of at least 5 hours (e.g., at least 5, 10, 12, 16, 18, 20, 24, 30, 48, 60, or 72 hours). In some embodiments, the epoxy resin compositions exhibit working time of from about 24 hours to about 48 hours. In some embodiments, the epoxy resin compositions exhibit working time of from about 24 hours to about 72 hours. In some embodiments, the epoxy resin compositions exhibit working time of from about 24 hours to about one week. In some embodiments, the epoxy resin compositions exhibit working time of from about 36 hours to about 48 hours. In some embodiments, the epoxy resin compositions exhibit working time of from about 36 hours to about 72 hours. In some embodiments, the epoxy resin compositions exhibit working time of from about 36 hours to about 1 week. In some embodiments, the epoxy resin compositions exhibit working time of from about 48 hours to about 72 hours. In some embodiments, the epoxy resin compositions exhibit working time of from about 48 hours to about 1 week. In some embodiments, the epoxy resin compositions exhibit working time of from about 48 hours to about 2 weeks.

The epoxy compositions described herein can be cured at between 30° C. to 220° C. In some embodiments, the epoxy compositions can be cured at between 50° C. to 170° C. In some embodiments, the epoxy compositions can be cured at least at 30° C., at least at 50° C., at least at 60° C., at least at 70° C., at least at 80° C., at least at 90° C., at least at 100° C., at least at 120° C., at least at 150° C., at least at 170° C., at least at 200° C., at least at 220° C. In some embodiments, the epoxy compositions can be cured at least at 80° C.

The epoxy compositions described herein should also find use in pipe repair applications (e.g., trenchless pipe repair applications). For example, the Cured in Place Pipe [CIPP] process involves inverting a resin saturated felt tube made of fiberglass and other materials inside a damaged pipe, and then curing the resin system, effectively making a pipe with in a pipe seal. Polyester thermosets, are commonly used for CIPP. For regulatory reasons, there is increasing momentum in the industry to switch a way from polyester resin systems, e.g., to epoxy-based systems. However, there has been a lack of suitable epoxy curatives that can be used for these purposes. The typical requirements of a resin systems are both that 1) the resin impregnated felt has to be easily pliable, e.g., for at last 24 hours after impregnation; and 2) the resin should cure in less than 24 hours (preferably less than 12 hours), e.g., at the temperature of the hot water passing through the pipe (usually <80° C.). Conventional epoxy curatives systems are not well suitable for either or both requirements. Curing with the sterically hindered amines described by Formula (1), enable epoxy resin compositions that satisfy both requirements.

For prepreg composite manufacturing, epoxy compositions must exhibit very slow cure rate at ambient temperature and/or cure to an intermediately stable state to be acceptable. This can be achieved with curing agents that cure the resin following a sequential course that entails, first, linear polymerization and subsequent cross-linking of the linear polymers. The polyamine cross-linking agents described herein are ideally suited for prepreg composite manufacturing. Epoxy resin compositions described herein provide long working time that keeps the epoxy resin composition flowing or manipulable for a long time and thus allows the epoxy composition to be shaped and processed over the long working time desired, e.g., for prepreg composite manufacturing. In some embodiments, the compositions are used for manufacturing prepreg composites.

Epoxy compositions described herein undergo (1) minimal reaction at ambient temperatures, but suitable reactivity at elevated temperatures; and (2) a slight linear polymerization which yields a glassy solid or metastable state, effectively slowing further linear polymerization or cross-linking, until reinitiated with introduction of energy, including heat at a higher temperature, to advance polymerization and cross-linking of the epoxy resin composition. One skilled in the art would recognize an epoxy composition in this metastable state as a "B-stage." One skilled in the art should also recognize that it is not typical for aliphatic polyamines curing agents to lead to B-staging epoxy resin compositions. As described herein, out-life or time in B-stage or B-state, are defined as the time to reach a partially cross-linked state (e.g., the time to reach a state wherein the epoxy composition is not capable of flowing, e.g., upon addition of elevated temperature; the time to reach a state wherein the epoxy composition is transformed to a partially or fully cross-linked polymer matrix).

In a typical prepreg process, an intermediate composite is formed, for example by coating a woven fiber (e.g. fiberglass, carbon fiber, aramid fiber, or natural fiber) with an epoxy resin and hardener mixture; and cured to an intermediate state. At the desired time, such prepreg sheets can be stacked and molded into a composite part by reestablishing the ductility of the epoxy composition and reinitiating the curing (e.g., by compression and heating). In order to make a good multilayered composite, the epoxy composition must be capable of "flow" for proper interpenetration between layers. The length of time a prepreg sheet can spend at room temperature before partial cross-linking of the epoxy resin composition occurs is known as the prepreg's "out-life." Premature cross-linking of a prepreg sheet effectively renders it useless for the manufacture of multilayered composites. After manufacturing, a prepreg sheet or roll may be stored in the freezer to extend its out-life prior to shipping or composite manufacture.

Generally, for an epoxy resin composition to be suitable for prepreg composite manufacturing, it should minimally have B-stage state of at least 1 week at room temperature. Ideally, the composition would have a B-stage state of infinity, however, in practice, commercial epoxy composition used in prepreg applications typically have a B-stage specification of months to 1 year.

Epoxy resin compositions described herein exhibit a B-stage state of at least 2 days at room temperature. In some embodiments, the epoxy resin compositions exhibit a B-stage state from about 2 days to about 1 week at room temperature. In some embodiments, the epoxy resin compositions exhibit a B-stage state from about 1 week to about 2 weeks at room temperature. In some embodiments, the epoxy resin compositions exhibit a B-stage state from about 2 weeks to about 1 month at room temperature. In some embodiments, the epoxy resin compositions exhibit a B-stage state from about 1 day, 2 days, 3 days, 4 days, 5 days, 6 days or more. In some embodiments, the epoxy resin compositions exhibit a B-stage state from about 1 week, 2 weeks, 3 weeks, 4 weeks, or more. In some embodiments, the epoxy resin compositions exhibit a B-stage state from about 1 month, 2 months, 3 months, 4 months, 5 months, 6 months, 7 months, 8 months, 9 months, 10 months, 11 months, or more. In some embodiments, the epoxy resin compositions exhibit a B-stage state from about 1 year, 2 years, or more. It should be understood by those skilled in the art, that the out-life of an epoxy resin compositions will be extended below room temperature, and shortened above room temperature.

Prepregs using the epoxy resin compositions described herein exhibit an out-life of at least 1 week at room temperature. In some embodiments, prepregs using the epoxy resin compositions exhibit an out-life of from about 1 week to about 2 weeks at room temperature. In some embodiments, prepregs using the epoxy resin compositions exhibit an out-life of from about 2 weeks to about 4 weeks at room temperature. In some embodiments, prepregs using the epoxy resin compositions exhibit an out-life of from about 1 day, 2 days, 3 days, 4 days, 5 days, 6 days or more. In some embodiments, prepregs using the epoxy resin compositions exhibit an out-life of from about 1 week, 2 weeks, 3 weeks, 4 weeks, or more. In some embodiments, prepregs using the epoxy resin compositions exhibit an out-life of from about 1 month, 2 months, 3 months, 4 months, 5 months, 6 months, 7 months, 8 months, 9 months, 10 months, 11 months, or more. In some embodiments, prepregs using the epoxy resin compositions exhibit an out-life of from about 1 year, 2 years, or more. Epoxy resin compositions described herein are suitable for use in the manufacture of electronic laminates that can be used in the manufacture of printed circuit boards [PCBs]. Printed circuit boards represent one of the largest single markets for epoxies. The worldwide PCB market is approximately 60 billion USD. Epoxy resin compositions account for nearly 1-2 billion in raw materials. PCBs account for nearly 3% of the 15 million tons of e-waste that is accumulated annually. Existing PCB disposal methods entail the manual removal of precious metal and then gridding of the laminate into filler. The development of inherently recyclable PCBs, as disclosed herein, would have clear environmental and economical benefits as the input materials could be recovered.

For composites applications that utilize prepreg and/or filament winding processes, there are effectively three types of curing agents that are widely used with epoxy resins: 1) DICY type curing agents (often in combination with imidazole accelerators); 2) anhydride-based curing agents (often in combination with imidazole accelerators); and 3) aromatic amines such as MDA and DDS. The use of aromatic amines, in particular MDA, has fallen out of favor in the industry due to toxicity concerns. Although aliphatic-type amines represent the most widely used epoxy curatives in the epoxy industry as a whole, they are generally unsuitable for use in filament winding and prepreg applications. The primary reason for this is that aliphatic amines are too reactive. The aliphatic polyamine cross-linking agents described herein react much more slowly than the aliphatic amines currently used in composites industry. Accordingly, epoxy resin compositions described herein, containing these aliphatic polyamine cross-linking agents are much more suitable for filament winding and prepreg applications.

Unlike thermoplastics, thermosetting plastics such as epoxies, are generally not recyclable. Cross-linking reactions that occur with conventional epoxies are essentially irreversible, which means the cross-linked materials cannot be re-melted and re-shaped without decomposition. Moreover, the cross-linked materials cannot be readily dissolved in most solvents. As a result, epoxy-based materials such as fiber reinforced epoxies or epoxy-based composite materials are generally not amenable to standard recycling practices. Thus, the epoxy matrix and fibers cannot be readily separated, and/or recovered. As result, such composite materials have historically been incinerated, land-filled, or ground and repurposed as filler material.

However, epoxy resin compositions described herein are recyclable even when cross-linked. The reason for this is that cross-linking groups in the cross-linked epoxy polymers are cleavable by chemical means, e.g., including reaction with acid. The aliphatic polyamine cross-linking agent described herein have at least one acetal or ketal group that is susceptible to cleavage under acidic conditions. Cross-linked epoxy polymers described herein contain these acid cleavable groups and therefore can be degraded for recycling purposes by treatment with acid.

The intractability of cured epoxy resins, stemming primarily, from their highly cross-linked network that is characteristic of known cured epoxy resins is not an issue with the cured epoxy resins described herein. Cured epoxy resins described herein can result in composites with links in a three-dimensional network structure which can be cleaved under controlled conditions, resulting in disassembly of the three-dimensional network structure into smaller, more soluble molecules and/or polymeric fragments. Degradable cured composites provide a way to recover any articles, reinforcement materials and the like that were in cured composite material. Replacing conventionally used epoxy hardeners with cleavable cross-linking agents described herein effectively solves the present recycling problem associated with epoxy based composites and materials.

The aliphatic polyamine cross-linking agents described herein are sterically hindered, reacting more slowly than conventional aliphatic-type polyamine cross-linking agents (e.g., non-sterically hindered polyamine cross-linking agents). As such epoxy resin compositions containing the aliphatic polyamine cross-linking agents described herein possess long working times, e.g., of sufficient length to make them useful in many applications, including filament winding applications. Epoxy resin compositions described herein provide reworkable epoxy compositions and thus composites made therefrom can be more easily degraded and recycled. Because of the slow reactivity of the aliphatic polyamine cross-linking agents described herein, epoxy resin compositions containing them exhibit an intermediate stable state that allows the epoxy composition to be processed over much longer working time than is possible with conventional hardeners. Accordingly, epoxy resin compositions described herein are useful for prepreg composite molding. Such composites can be recycled because the prepreg composites are reworkable by methods described herein.

Examples of sterically hindered aliphatic polyamine cross-linking agents described herein include compounds of the Formula (1). In some embodiments, sterically hindered aliphatic polyamine cross-linking agents described herein include, but are not limited to, the following exemplary compounds.

Formula (1-1)

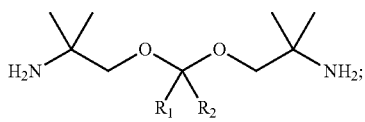

wherein each of $R^1$ and $R^2$ is independently selected from the group consisting of hydrogen, alkyl group, cycloalkyl group and aromatic group; and $R^1$ and $R^2$ together with the carbon atom to which they are attached form a cyclic ring. In some embodiments, the compound of Formula (1-1) is:

H-(1-1)

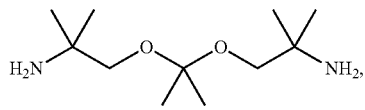

H-(1-2)

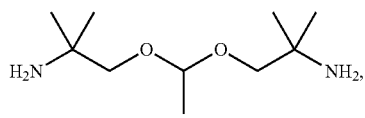

H-(1-3)

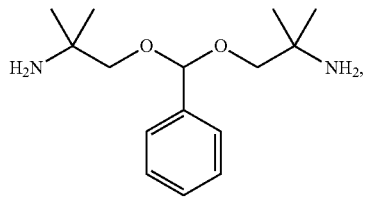

H-(1-4)

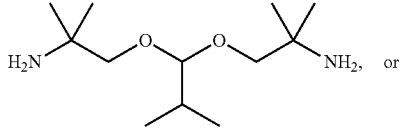

or

H-(1-5)

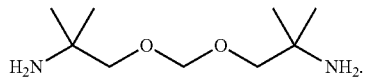

Terms such as "hardenable" or "curable" are used interchangeably herein, and are intended to refer to any material that can be stably stored for an extended period of time in a first, malleable or flexible form without loss of flexibility, and transitionable into a second, hardened form after application of an initiating energy thereto. These terms are not intended to be limited to any specific mechanism of hardening. As will be understood by those of skill in the art, a variety of hardening mechanisms can be utilized, depending upon material selection, including for example, curing that is initiated by ultraviolet radiation, visible light, infrared radiation, radio frequency radiation, x-ray radiation, gamma radiation or other wavelength of electromagnetic energy, catalyst-initiated polymerization, thermally-initiated polymerization, electrically-initiated polymerization, mechanically-initiated polymerization, curing initiated by electron beam radiation and the like.

Formula (1) represents a class of polyamine molecules that depending on the exact nature of $R^1$ and $R^2$ can be subdivided into three classes: (i) polyaminoformal ($R^1$=H; and $R^2$=H); (ii) polyaminoacetal (e.g., $R^1$=H; and $R^2$=carbon fragment); and (ii) polyaminoketal (e.g., $R^1$=carbon fragment; and $R^2$=carbon fragment). Individually, the molecules classified according to Formula (1) may contain an acetal group, ketal group, or a formal group, that connects the polyamine groups.

Referring to the compounds of Formula (1), in one embodiment, each of $R^1$ and $R^2$ is independently an alkyl group. In one embodiment, each of $R^1$ and $R^2$ is independently a $C_1$-$C_{20}$ alkyl group. In one embodiment, each of $R^1$ and $R^2$ is independently a $C_1$-$C_{15}$ alkyl group. In one embodiment, each of $R^1$ and $R^2$ is independently a $C_1$-$C_{10}$ alkyl group. In one embodiment, each of $R^1$ and $R^2$ is independently a $C_1$-$C_5$ alkyl group. In one embodiment, each of $R^1$ and $R^2$ is independently a $C_1$-$C_3$ alkyl group. In one embodiment, each of $R^1$ and $R^2$ is independently a $C_1$-$C_2$ alkyl group. In one embodiment, each of $R^1$ and $R^2$ is independently a $C_1$ alkyl group. In one embodiment, each of $R^1$ and $R^2$ is independently selected from the group consisting of $C_1$ (e.g., methyl); $C_2$ (e.g., ethyl); $C_3$ (e.g., propyl); $C_4$ (e.g., n-butyl & isobutyl); $C_5$ (e.g., pentyl, isopentyl, neopentyl); and $C_6$ (e.g., hexyl, 2-Methylpentyl; 3-Methylpentyl; 2,3-Dimethylbutyl; 2,2-Dimethylbutyl). In one embodiment, each of $R^1$ and $R^2$ is independently selected from the group consisting of methyl, ethyl, propyl, isopropyl, butyl, isobutyl, tert-butyl, amyl, isoamyl, pentyl, sec-butyl, isopentyl, neopentyl, heptyl, hexyl, octyl, decyl, dodecyl, and hexadecyl. In one embodiment, each of $R^1$ and $R^2$ is independently selected from the group consisting of methyl, ethyl, propyl, butyl, pentyl, hexyl, heptyl, octyl, nonyl, decyl, undecyl, dodecyl, hexadecyl, and icosyl. In one embodiment, each of $R^1$ and $R^2$ is independently methyl. In one embodiment, each of $R^1$ and $R^2$ are both methyl.

In one embodiment, each of $R^1$ and $R^2$ is independently a cycloalkyl group. In one embodiment, each of $R^1$ and $R^2$ is independently a cycloalkyl group. In one embodiment, each of $R^1$ and $R^2$ is independently a $C_3$-$C_{20}$ cycloalkyl group. In one embodiment, each of $R^1$ and $R^2$ is independently a $C_3$-$C_{15}$ cycloalkyl group. In one embodiment, each of $R^1$ and $R^2$ is independently a $C_3$-$C_{10}$ cycloalkyl group. In one embodiment, each of $R^1$ and $R^2$ is independently a $C_3$-$C_5$ cycloalkyl group. In one embodiment, each of $R^1$ and $R^2$ is independently selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

In one embodiment, each of $R^1$ and $R^2$ is independently an aryl group. The term "aryl" as used herein refers to any functional group or substituent derived from an aromatic ring, be it phenyl, naphthyl, thienyl, indolyl, or the like. Examples of aryl include, but are not limited to, phenyl, tolyl, xylyl, naphthyl, biphenylyl, benzyl, and phenylethyl groups.

In one embodiment, $R^1$ and $R^2$ together with the carbond atom to which they are attached form a cyclic group. The cyclic group is not particularly limited. It can be a carbocycle, a cycloalkyl, an aryl, a heterocycle, a heteroaryl, an aralkyl or any suitable cyclic group. In one embodiment, the cyclic group is selected from the group consisting of cycloalkyl, cycloalkyl aryl, heterocyclic, alkylaryl, alkylheterocycle and arylheterocycle groups.

In one embodiment, each of $R^3$ and $R^4$ is independently an alkyl group. In one embodiment, each of $R^3$ and $R^4$ is independently a methyl group. In one embodiment, $R^3$ and $R^4$ are both an alkyl group. In one embodiment, $R^3$ and $R^4$ are both methyl.

In one embodiment, each of $R^3$ and $R^4$ is independently a $C_1$-$C_{20}$ alkyl group. In one embodiment, each of $R^3$ and $R^4$ is independently a $C_1$-$C_{15}$ alkyl group. In one embodiment, each of $R^3$ and $R^4$ is independently a $C_1$-$C_{10}$ alkyl group. In one embodiment, each of $R^3$ and $R^4$ is independently a $C_1$-$C_5$ alkyl group. In one embodiment, each of $R^3$ and $R^4$ is independently a $C_1$-$C_3$ alkyl group. In one embodiment, each of $R^3$ and $R^4$ is independently a $C_1$-$C_2$ alkyl group. In one embodiment, each of $R^3$ and $R^4$ is independently a $C_1$ alkyl group. In one embodiment, each of $R^3$ and $R^4$ is independently selected from the group consisting of $C_1$ (e.g., methyl); $C_2$ (e.g., ethyl); $C_3$ (e.g., propyl); $C_4$ (e.g., n-butyl & isobutyl); $C_5$ (e.g., pentyl, isopentyl, neopentyl); and $C_6$ (e.g., hexyl, 2-Methylpentyl; 3-Methylpentyl; 2,3-Dimethylbutyl; 2,2-Dimethylbutyl). In one embodiment, each of $R^3$ and $R^4$ is independent selected from the group consisting of methyl, ethyl, propyl, isopropyl, butyl, isobutyl, tert-butyl, amyl, isoamyl, pentyl, sec-butyl, isopentyl, neopentyl, heptyl, hexyl, octyl, decyl, dodecyl, and hexadecyl. In one embodiment, each of $R^3$ and $R^4$ is independent selected from the group consisting of methyl, ethyl, propyl, butyl, pentyl, hexyl, heptyl, octyl, nonyl, decyl, undecyl, dodecyl, hexadecyl, and icosyl.

In one embodiment, each of $R^3$ and $R^4$ is independently a cycloalkyl group. In one embodiment, each of $R^3$ and $R^4$ is independently a cycloalkyl group. In one embodiment, each of $R^3$ and $R^4$ is independently a $C_3$-$C_{20}$ cycloalkyl group. In one embodiment, each of $R^3$ and $R^4$ is independently a $C_3$-$C_{15}$ cycloalkyl group. In one embodiment, each of $R^3$ and $R^4$ is independently a $C_3$-$C_{10}$ cycloalkyl group. In one embodiment, each of $R^3$ and $R^4$ is independently a $C_3$-$C_5$ cycloalkyl group. In one embodiment, each of $R^3$ and $R^4$ is independently selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

In one embodiment, each of $R^3$ and $R^4$ is independently an aryl group. As stated elsewhere herein, the term "aryl" refers to any functional group or substituent derived from an aromatic ring, be it phenyl, naphthyl, thienyl, indolyl, or the like. Examples of suitable aryl groups include, but are not limited to, phenyl, tolyl, xylyl, naphthyl, biphenylyl, benzyl, and phenylethyl groups.

In one embodiment, $R^3$ and $R^4$ together with the carbon atom to which they are attached form a cyclic ring. In one embodiment, $R^3$ and $R^4$ together with the carbon atom to which they are attached form a $C_3$-$C_{20}$ cycloalkyl group. In one embodiment, $R^3$ and $R^4$ together with the carbon atom to which they are attached form a $C_3$-$C_{15}$ cycloalkyl group. In one embodiment, $R^3$ and $R^4$ together with the carbon atom to which they are attached form a $C_3$-$C_{10}$ cycloalkyl group. In one embodiment, $R^3$ and $R^4$ together with the carbon atom to which they are attached form a $C_3$-$C_5$ cycloalkyl group. In one embodiment, $R^3$ and $R^4$ together with the carbon atom to which they are attached form a cyclic group selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

Each m and n in the polyamine compounds represented by Formulas (1) is independently an integer ranging from 1 to 20. In one embodiment, each m and n is independently an integer selected from the group consisting of 1, 2, 3, 4, 5, 6, 7, 8, 9, 10, 11, 12, 13, 14, 15, 16, 17, 18, 19, and 20. In one embodiment, each m and n is 1.

In one embodiment, the epoxy resin composition comprises an epoxy resin that has an average of at least two epoxide groups per molecule. In one embodiment, the epoxy resin composition comprises a diepoxide resin. In one embodiment, the epoxy resin composition comprises a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin, and combinations thereof.

In some embodiments, the epoxy resin composition comprises an epoxy resin that comprises a blend of epoxy resins. In one embodiment, the epoxy resin composition comprises a blend of bisphenol-based epoxy resins. In one embodiment, the epoxy resin composition comprises a blend of bisphenol-based epoxy resins having an epoxide equivalent weight (EEW) in the range of 160 to 220. In one embodiment, the epoxy resin composition comprises a blend of bisphenol-based epoxy resins having an epoxide equivalent weight (EEW) in the range of 400 to 1500.

In some embodiments, epoxy resins may be blended, filled, or modified with reactive and non-reactive components. In one such embodiment, it may be necessary to adjust the concentration of the curing polyamine agent to cure only the portion of the mix that is reactive; e.g., the resins and any reactive diluent present. In one embodiment, this may be done by calculating the epoxide equivalent weight (EEW) of the total mix and then applying equation 2 (eq. 2) to determine the amount of curing polyamine agent to add to 100 parts of the epoxy resin composition. As an example, an EEW of a blended epoxy resins may be calculated according to equation 4 (eq.4).

$$EEW \text{ of mix} = \frac{(\text{Total Wt. of Mix})}{(Wta/(EEWa) + Wtb/(EEWb) + \ldots + Wtn/(EEWn))} \quad (\text{eq. 4})$$

wherein Total Wt. of Mix represents the molecular weight of the total mix and includes all materials, both reactive and non-reactive; a, b, . . . and n, are only the materials reactive with the aliphatic polyamine cross-linking agent and are characterised by an epoxy ring; EEWa represents EEW of reactive material a; EEWb represents EEW of reactive material b; and EEWn represents EEW of reactive material n.

In some embodiments, the epoxy resin composition includes a blended epoxy resin, and an aliphatic polyamine cross-linking agent of Formula (1) as can be calculated by eq.3 above. In one embodiment, epoxy resin blend includes a mixture of a diglycidyl ether of a bisphenol, especially bisphenol A, having an EEW of 150-195, typically 180-190, and a diglycidyl ether of a bisphenol, especially bisphenol A having an EEW of 400-1500, preferably 1200-1400. In one embodiment, epoxy resin blend includes a mixture of a diglycidyl ether of a bisphenol, especially bisphenol A, having an EEW of 150-195, typically 180-190, a diglycidyl ether of a bisphenol, especially bisphenol A, having an EEW of 400-1500, preferably 1200-1400, and an epoxy phenolic novalac resin with a functionality of 2.2 to 4, typically 3.6 or above, having an EEW of 170-190, preferably 174-180. In one embodiment, epoxy resin blend includes a mixture of a diglycidyl ether of a bisphenol, especially bisphenol A, having an EEW of 150-195, typically 176, a diglycidyl ether of a bisphenol, typically bisphenol A, having an EEW of 400-1500, preferably 1200-1400, and a tetra-functional epoxy having an EEW of 117-134.

Various bisphenol-based epoxy resin blends may be used to make compositions described herein. In particular, in one embodiment the bisphenol-based epoxy resin is a blend based on the reaction products of epichlorohydrin and bisphenol A ("BPA") and/or bisphenol F ("BPF"). Bisphenol-based epoxy resins that are useful include, but are not limited to, bisphenol A diglycidyl ether, ("BPADGE") and its oligomers and bisphenol F diglycidyl ether, ("BPFDGE") and its oligomers. FIG. 2 depicts various epoxy resins including generic structures for BPADGE and BPFDGE and their oligomers. In some embodiments, molecular weight of preferred oligomers of BPADGE and BPFDGE can be up to approximately 6000 g/mol. In one embodiment, the bisphenol-based epoxy resin based on bisphenol A has a molecular weight in the range of about 340 to about 6000 g/mol. In one embodiment, the bisphenol-based epoxy resin based on bisphenol F has a molecular weight in the range of about 310 to about 6000 g/mol. In some embodiments, the bisphenol-based epoxy resins have a molecular weight between and optionally including any two of the following values: 298, 300, 310, 340, 400, 600, 800, 1000, 1200, 1500, 1800, 2100, 2400, 2700, 3000, 3300, 3600, 3900, 4200, 4500, 4800, 5100, 5400, and 6000. Since the bisphenol-based epoxy resins have 2 epoxy groups per oligomer, the bisphenol-based epoxy resins have an epoxide equivalent weight (EEW) that is generally about half of the molecular weight of the oligomer. In one embodiment, the bisphenol-based epoxy resin is present from about 40 to about 95 wt %, based on the combined weight of the bisphenol-based epoxy resin, amine curing agent, and multi-epoxy reactive diluents. In another embodiment, the bisphenol-based epoxy resin is present from about 40 to about 95 wt %, based on the combined weight of the components in the curable composition. In some embodiments, the bisphenol-based epoxy resin is present in an amount between and optionally including any two of the following values: 40, 45, 50, 55, 60, 65, 70, 75, 80, 85, 90, and 95 wt %, based on the combined weight of the components in the curable composition. In some embodiments, the bisphenol-based epoxy resin is contains bromine atoms. Brominated epoxy resins are useful for applications that require flame retardency Specific, but non-limiting, examples of commercially available bisphenol A diglycidyl ether epoxy resins are Insulcast 503/504 BLK; Insulcast 504 Clear; Insulcast 125; Insulcast 333; Insulcast 136; and Insulcast 502, available (from ITW Polymer Technologies (Glenview, Ill., U.S.A.); Epon resins from Hexion Specialty Chemicals, Inc., now Momentive Specialty Chemicals, Inc., part of Momentive Performance Materials Holdings, Inc., (Columbus, Ohio, U.S.A.); D.$^E$® resins from The DOW Chemical Company. Specific, but non-limiting, examples of commercially available include bisphenol F diglycidyl ether epoxy resins, including Araldite® GY285, Araldite® GY281, and Araldite® PY302-2 from Huntsman International, LLC (Salt Lake City, Utah, USA). Mixtures of bisphenol-based epoxy resins can be used in the curable composition described herein.

In some embodiments, reactive diluents are added to a bisphenol-based epoxy resin. In some embodiments, monofunctional epoxides are further blended with the bisphenol-based epoxy resin. Reactive diluents are common additives for influencing the viscosity of resin systems. Reactive diluents can also improve the surface qualities of coatings and composites. Specific, but non-limiting, examples of suitable reactive diluents include, $C_{12}$-$C_{14}$ alkyl glycidylethers, o-cresyl glycidylether, and butyl-glycidylether.

In some embodiments, a less than stoichiometric amount of polyamine curing agent of Formula (1) is used in the epoxy resin composition described herein. In one embodiment, the epoxy resin composition contains 2% of the stoichiometric amount of polyamine curing agent of Formula (1). In one embodiment, the epoxy resin composition contains the aliphatic polyamine cross-linking agent of Formula (1) in a percentage selected from the group consisting of about 4%, about 6%, about 8%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, and about 98% of the stoichiometric amount of polyamine curing agent of Formula (1). In one embodiment, the epoxy resin composition contains the aliphatic polyamine cross-linking agent of Formula (1) in a percentage selected from the group consisting of less than about 4% but greater than about 2%, less than about 6% but greater than about 2%, less than about 8% but greater than about 2%, less than about 10% but greater than about 2%, less than about 12% but greater than about 2%, less than about 14% but greater than about 2%, less than about 16% but greater than about 2%, less than about 18% but greater than about 2%, less than about 20% but greater than about 2%, less than about 22% but greater than about 2%, less than about 24% but greater than about 2%, less than about 26% but greater than about 2%, less than about 28% but greater than about 2%, less than about 30% but greater than about 2%, less than about 32% but greater than about 2%, less than about 34% but greater than about 2%, less than about 36% but greater than about 2%, less than about 38% but greater than about 2%, less than about 40% but greater than about 2%, less than about 42% but greater than about 2%, less than about 44% but greater than about 2%, less than about 46% but greater than about 2%, less than about 48% but greater than about 2%, less than about 50% but greater than about 2%, less than about 52% but greater than about 2%, less than about 54% but greater than about 2%, less than about 56% but greater than about 2%, less than about 58% but greater than about 2%, less than about 60% but greater than about 2%, less than about 62% but greater than about 2%, less than about 64% but greater than about 2%, less than about 66% but greater than about 2%, less than about 68% but greater than about 2%, less than about 70% but greater than about 2%, less than about 72% but greater than about 2%, less than about 74% but greater than about 2%, less than about 76% but greater than about 2%, less than about 78% but greater than about 2%, less than about 80% but greater than about 2%, less than about 82% but greater than about 2%, less than about 84% but greater than about 2%, less than about 86% but greater than about 2%, less than about 88% but greater than about 2%, less than about 90% but greater than about 2%, less than about 92% but greater than about 2%, less than about 94% but greater than about 2%, less than about 96% but greater than about 2%, and less than about 98% but Hardeners described herein (e.g., H-(1-1), H-(1-2), H-(1-3), H-(1-4), and H-(1-5)), are relatively low viscosity liquids. Low viscosity may provide some processing advantages over the currently used "latent" epoxy curing agents used in the art of composites, (e.g., aromatic amines and DICY/Imidazole type curatives are typically solids). H-(1-1), H-(1-2), H-(1-3), H-(1-4), and H-(1-5) can be prepared using known methods as, for example, in U.S. Pat. No. 2,363,464. The properties of specific hardeners described herein, as well as a cured epoxy composition consisting of a bisphenol A-type epoxy resin (e.g., under the trade name EPON 828 (EEW=188)) and compounds (of the Formula (1)) are provided in the following Table 1:

TABLE 1

| Hardener | H-(1-1) | H-(1-2) | H-(1-3) | H-(1-4) | H-(1-5) |
|---|---|---|---|---|---|
| AEW | 55 | 51 | 67 | 58 | 47.5 |
| Formulation with EPON 828 epoxy resin (EEW 188) | | | | | |
| PPH amine | 29 | 27 | 36 | 31 | 25 |
| Working Time (125 g mass, 22° C.) | 32-48 h | 32-48 h | 32-48 h | 32-48 h | 32-48 h |
| Mixed viscosity (5 min), 25° C. | 1200 cP | 906 cP | 3300 cP | 1165 cP | 725 cP |
| Gel time$^a$ | | | | | |
| 100° C. | 35 min | 47 min | 45 min | 57 min | 41 min |
| 150° C. | 3.1 min | 2.4 min | 3.3 min | 5.6 min | 1.3 min |
| $^b$Elevated Temperature Cure, 2 hr 100° C. then 4 h @ 140° C. | | | | | |
| Tg | 116° C. | 114° C. | 119° C. | 109° C. | 111° C. |
| Tensile Strength, psi | 10,630 | 10,720 | 12,430 | 10,540 | 10,610 |
| Tensile Modulus, psi | 498,140 | 483,400 | 503,900 | 479,780 | 445,400 |
| Elongation at break | 6.2% | 5.8% | 6.1% | 6.4% | 8.6% |
| Flexural Strength, psi | 15,130 | 15,790 | 19,760 | 15,070 | 14,800 |
| Flexural Modulus | 412,960 | 445,200 | 495,600 | 419,080 | 407,100 |
| Weight Gain$^c$ | | | | | |
| Water, 24 hr Boil | 0.9-1.5% | 0.9-1.5% | 0.9-1.5% | 0.9-1.5% | 10.9-1.5% |
| 5% Acetic acid, 7 Day immersion | 0.2% | 0.2% | 0.2% | 0.2% | 0.3% |
| Dissolution Half life (Recycling)$^c$ | | | | | |
| 25% Acetic Acid in water @ 100° C. | 73 min | 720 min | 313 min | 24 hr to fully dissolve | +16.5% weight gain |
| 10% HCl in ethylene glycol @ 120° C. | 73 min | 78 min | 72 min | 103 min | >2 day to fully dissolve |

$^a$ determined via rheometry
$^b$Tensile and flexural Properties determined via ASTM standards; Tg determined using DSC
$^c$standard samples (20 g discs; 4 mm thickness)
PPH refers to the parts (e.g., of amine) per hundred parts of the resin.

greater than about 2% of the stoichiometric amount of polyamine curing agent of Formula (1).

For a given epoxy composition and application, the ideal amount of the sterically hindered, reworkable curing agent of Formula (1) may be less than, or greater than the calculated stoichiometric amount. One skilled in the art can recognize that deviations from the stoichiometric amount may lead to changes in the processing properties of the epoxy composition or of the final properties of the cured thermoset. Such changes may, or may not, be desired depending on the manufacturing method employed or the end application for the epoxy-based material. The preferable amount can be easily determined by one skilled in the art via routine experimentation, but is preferably in the range of about 60% to about 140% of the stoichiometric amount, and more preferably from about 90% to about 110%.

The curable resin composition described herein is obtained by uniformly mixing the above-described components. A process of obtaining a cured product described herein from the curable resin composition described in detail above may be in accordance with a commonly used curing process of a curable resin composition. The heating temperature condition can be appropriately selected in accordance with the type of curing agent used in the combination or application. In an example of the process, the curable resin composition described herein is heated in the temperature range of about 20° C. to 250° C. Examples of the form of the cured product include a laminate, a cast product, an adhesive layer, a coating film, and a film.

Table A, below provides a comparison of working times of industrial aliphatic amines and Formula (1) amines

TABLE A

Comparison of working times of industrial aliphatic amines and Formula (1) amines Formulated with standard DGEBA (EEW = 180-195) resins

| Aliphatic amine class | Common or Trade name | Molecular structure | Working time (gel time) |
|---|---|---|---|
| Polyetheramine | Jeffamine ®D-230 | $H_2N\text{—}CHCH_2O\text{—}(H_2CHO)_x\text{—}CH_2CH\text{—}NH_2$ with $CH_2$, R, $CH_2$ substituents; X = 1,2 | 280 min |
| Cycloaliphatic | Isophorone diamine (IPDA) | 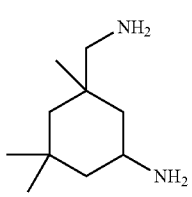 | (128 min) |
| Cycloaliphatic | 4,4'-Diaminodicyclohexyl methane (PACM) | 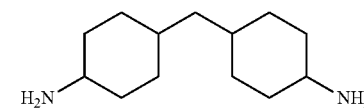 | 220 min (93 min) |
| polyethyleneamine | Diethylenetriamine DETA | 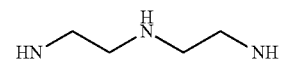 | <30 Min |
| Sterically hindered acetal/ketal | Formula (1) | 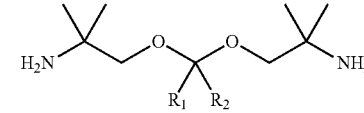 | 0.5-2 day |

Filament winding generally consists of forming a resin mixture bath, immersion of a glass, carbon, aramid, natural, unnatural fiber (of from about 1-3 mm in diameter) in the mixture for a period of time (typically for about 1 sec), winding the wet fiber on a mandrel, and, subsequently, further curing with heat the composite, which includes the resin mixture and the fiber. The gel times of resin mixtures described herein are sufficiently long for filament winding purposes. The working time for stoichiometric mixtures of DGEBA with Hardeners (e.g., H-(1-1), H-(1-2), H-(1-3), H-(1-4), and H-(1-5)) are greater than 24 hrs. At room temperature (i.e. 20-25° C.), the resin mixtures become a hard brittle solid between 30-48 hours (the intermediate state). Upon heating the intermediate state, the mixture will melt, and then harden again when cross-linking. This characteristic may also be obtained with epoxy compositions that contain auxiliary agents, such as fillers and fibers. This type of curing behavior is atypical for the aliphatic amines used in composite manufacturing such as isophorone diamine, Jeffamines® hardeners and other cycloaliphatic-type, polyethyleneamine-type, and polyetheramine-type epoxy hardeners. In some embodiments, the curing agents described are sterically hindered. The Formula (1) hardeners H-(1-1), H-(1-2), H-(1-3), H-(1-4), and H-(1-5), are sterically hindered, e.g., containing a geminal dimethyl groups attached to an amine baring carbons. The intermediate state was found to be stable for up to one week at room temperature when using epoxy resins with an low EEW (i.e., EEW<200). The stability of the intermediate state increases significantly with epoxies with high EEW (i.e. >500). As a result, the blending of epoxy resins with different EEW values can be used to further tailor the "latency" of the epoxy composition. For example, in an epoxy composition comprising a 50/50 weight ratio blend of EPON 828 (EEW=188) and EPON 1001 (EEW=500); and the stoichiometric amount of the sterically hindered hardener H-(1-1), the intermediate state was stable for more than 3 months. The composition was meltable and then cross-linked by heating of the intermediate state. This curing behavior is consistent with the primary amines having reacted with resin (linear polymerization) prior to the secondary amines having reacted (cross-linking). This curing behavior makes the sterically hindered diamine as embodied by compounds of type Formula (1) useful, e.g., for prepregs.

Unless otherwise stated herein, the terms "hardener", "curing agent", "cross-linking agent" are used interchangeable as synonyms of "cross-linking agent". As is the case with thermosetting epoxies, the processing properties (e.g. curing time, peak exotherm, mixed viscosity, etc.) and cured resin physical properties (Tg, tensile strength, flexibility modulus, chemical resistance, conductivity, adhesion, color, impact strength, etc.) can be modified by the addition of auxiliary materials to the base epoxy resin/hardener composition for the purposes of preparation of epoxy compositions tailored for a given application. Accordingly, in some embodiments, the epoxy resin composition further includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive and combinations thereof.

In some embodiments, amino molecules that contain 2, or less than 2, active N—H hydrogens can be used in combination with the aliphatic polyamine cross-linking agents of Formula (1). Primary monoamines, bis(secondary) diamine molecules, and other molecules that contain only two active N—H hydrogens are suitable for use in the epoxy resin composition described herein, e.g., as chain extenders. In one embodiment, the chain extenders are used to adjust the cross-link density of a cured epoxy resin in accordance with exemplary embodiments described herein. By adding these chain extenders to the polyamine curing agents of Formula (1), one can decrease the cross-linking density in the final cured epoxy matrix. Specific, but non-limiting, examples of chain-extendable molecules that contain only two active N—H hydrogens include monoethanolamine, 3-aminopropanol, 2-aminopropanol, 2-amino-2-methyl-1-propanol [AMP], benzylamine, aniline, p-anisidine, butylamine, piperazine, and N,N'-dimethylethylenediamine, tert-butylamine, and, sec-butylamine. In an embodiment, the epoxy resin composition described herein includes at least one amine chain extender in an amount ranging from about 0% to about 98% relative to weight of the aliphatic polyamine cross-linking agent of Formula (1).

One skilled in the art will recognize that the incorporation of chain extenders will alter the processing and mechanical properties of the epoxy composition from that of an epoxy composition that only uses Formula (1) as the reactive curing agent. In one embodiment, 2-amino-2-methyl-1-propanol [AMP] is preferred as a chain extender, e.g., because its combination with polyamine curing agent of Formula (1) does not alter the molecular formula of the recovered epoxy thermoplastic after recycling. In particular, the use of amino alcohols also has the effect of as an accelerator. For example, amino alcohols elevate temperature gel time of a epoxy composition consisting of a bisphenol A-type epoxy resin (EEW=188) and, for example, H-(1-1) (AEW=51), and amino alcohol AMP (AEW=22), and gave the following exemplary results shown on Table 2:

TABLE 2

| Parts Resin | Parts H-(1-2) | Parts AMP | Equivalence of AMP | Gel Time at 115° C. |
|---|---|---|---|---|
| 100 | 27 | 0 | 0% | 27 minutes |
| 200 | 24.3 | 2.4 | 10% | 20 minutes |

In some embodiments, conventional, polyamino molecules that contain greater than 2 N—H hydrogens are used in combination with polyamine curing agents of Formula (1). The composition (e.g., formulation) of conventional epoxy curing agents with the polyamine curing agent of Formula (1) will increase the amount of non-degradable cross-links in the final cured epoxy matrix. This action will be, generally, detrimental to the removal and/or recycling of the epoxy composition; however may find use in applications where partial degradation is desired. In one embodiment, non-degradable polyamines in an amount of from about 1 wt. % to 25 wt. % is combined with the polyamine curing agent of Formula (1), e.g., to increase the amount of non-degradable cross-links in the final cured epoxy matrix. In one embodiment, non-degradable polyamine in an amount selected from the group consisting of about 1 wt. % to about 25 wt. %, about 2 wt. % to about 25 wt. %, about 3 wt. % to about 25 wt. %, about 4 wt. % to about 25 wt. %, about 5 wt. % to about 25 wt. %, about 6 wt. % to about 7 wt. %, about 8 wt. % to about 25 wt. %, about 9 wt. % to about 25 wt. %, about 10 wt. % to about 25 wt. %, about 11 wt. % to about 25 wt. %, about 12 wt. % to about 25 wt. %, about 13 wt. % to about 25 wt. %, about 14 wt. % to about 25 wt. %, about 15 wt. % to about 25 wt. %, about 16 wt. % to about 25 wt. %, about 17 wt. % to about 25 wt. %, about 18 wt. % to about 25 wt. %, about 19 wt. % to about 25 wt. %, about 20 wt. % to about 25 wt. %, about 21 wt. % to about 25 wt. %, about 22 wt. % to about 25 wt. %, about 23 wt. % to about 25 wt. %, and about 24 wt. % to about 25 wt. % of the epoxy composition is combined with the polyamine curing agent of Formula (1), e.g., to increase the amount of nondegradable cross-links in the final cured epoxy matrix. Specific, but non-limiting examples of conventional polyamines include polyetheramines and ethyleneamines; and cycloaliphatic and aromatic classes of diamino and/or polyamino molecules.

In some embodiments, the epoxy resin composition further includes a reinforcing agent. In one embodiment, the reinforcing agent is selected from a group consisting of glass fiber, carbon fiber, carbon nanotube fiber, cellulose fiber, natural fiber, chemical fiber, and non-natural fiber. The fiber may be woven or non-woven, unidirectional or multi-directional, chopped matt or any combination thereof. The methods described herein is not limited to the method of applying the epoxy resin composition to the fiber. For example, infusion, wet lay-up, resin transfer molding, vacuum bagging, and other standard composite techniques may also be used In some embodiments, the epoxy resin composition further includes a non-fiber reinforcing agent. Specific, but non-limiting, examples, of non-fiber reinforcing agents include carbon nanotube, carbon black, metal nanoparticle, organic nanoparticle, iron oxide, boron nitride, and combinations thereof.

Printed circuit boards [PCBs] represent one of the largest single markets for epoxies. The worldwide PCB market is approximately 60 billion USD. Epoxy resin compositions account for nearly 1-2 billion USD in raw materials. PCBs account for nearly 3% of the 15 million tons of e-waste that is accumulated annually. Existing PCB disposal methods entail ii) manual removal of precious metal and then gridding of the laminate into filler. The development of inherently recyclable PCBs would have clear environmental and economical implications as the input materials could be recovered. Commercially aliphatic polyamine hardeners are not conventionally used as the curing agents for epoxy compositions for printed circuit boards application because, e.g., 1) they cure too rapidly to be useful in prepreging; and 2) they do not have high enough glass transition temperatures for PCB requirements.

Laminates for PCB applications are manufactured via a process known as prepreging. A typical procedure for forming prepregs and laminates for printed circuit boards involve such operations as:

A) An epoxy composition (e.g., formulation) is applied to or impregnated into a substrate by rolling, dipping, spraying, other known techniques and/or combinations thereof. The substrate maybe an inorganic or organic reinforcing agent in the form of fibers, fleece, fabric or textile material (e.g., typically a woven or non-woven fiber mat containing, for example, glass fibers or paper).

B) The impregnated substrate is "B-staged" by heating at a temperature sufficient to draw off solvent in the epoxy composition (e.g., formulation) and optionally to partially cure the epoxy composition (e.g., formulation), so that the impregnated substrate is dry to the touch (i.e. "tack-free") and can be handled easily. The B-staging step is usually carried out with temperature of from 21° C. to 90° C. The impregnated substrate that results from B-Staging is commonly referred to as a "prepreg."

C) One or more sheets of prepreg are stacked or laid-up in alternating layers with one or more sheets of a conductive materials, such as copper foil, if an electrical laminate is desired.

D) The laid-up sheets are pressed at high temperature and pressure for a time sufficient to fully cure the epoxy composition and form a laminate. The temperature of this lamination step is usually between 100° C. and 230° C., and is most often between 165° C. and 190° C. The pressure is usually between 50 N/cm$^2$ and 500 N/cm$^2$. The lamination step is usually carried out for a time of from 1 minutes to 200 minutes, and most often between 20 minutes to 90 minutes. The lamination step may optionally be carried out at higher temperatures for shorter times (such as in continuous lamination processes) or for longer times at lower temperatures (such as in low energy press processes).

E) Optionally, the resulting laminate, for example, a copper-clad laminate, may be post-treated for a time at high temperature and ambient pressure. The temperature of post-treatment is usually between 120° C. and 250° C. The post-treatment usually is between 30 minutes and 12 hours.

F) Often an electrically conductive printed circuit is applied to the copper-clad laminate.

There are also other methods that are used to make prepregs and laminates for PCB applications, such as hot melt method where a b-staged epoxy is melted and pressed on to the reinforcement substrate.

Regardless of the method for preparation of the laminate, the hardener requirements for epoxy compositions for use in PCB applications must meet very specific requirements in order to be suitable for prepreg manufacture. The curing speed of the hardener is one critical component. In order to be suitable, it should only react slowly with epoxy in the ambient temperature. If the hardener system employed does not possess such "latency", the B-Staged resin may pass into a cross-linked state (C-staged) prior to making the laminate. A C-staged resin will not be able to melt or flow, and therefore, stacking and hot-pressing prematurely C-staged prepregs will prevent proper interpenetration of the epoxy between sheets. In addition to processing requirements, epoxy curatives for PCB application must also meet very specific electrical, thermal, and mechanical criteria, such as dielectric constant, dissipation factor, high Tg, high thermal decomposition temperature, low moisture uptake, etc. DICY type curing agents (often in combination with imidazole accelerators), anhydride-based curing agents (often in combination with imidazole accelerators), and aromatic amines such as MDA and DDS have been the standard epoxy curing agents for PCB applications. These hardeners possess sufficient latency to be used in a prepreg process, and also produce cured resins with sufficient physical, electrical, and thermal properties for electronic applications. These standard hardeners are often used in combination with various additives such as Tg enhancers, flame retardants, and other auxiliary agents that enhance the mechanical, thermal, and/or electrical properties of the final laminate, flexiblizers (i.e. silicone based epoxy resins). The use of aromatic amines, in particular MDA, has fallen out of favor in the industry due to toxicity concerns. Although aliphatic-type amines represent the most widely used epoxy curatives in the epoxy industry as a whole, they are generally unsuitable for use in epoxy resin PCB applications. Aliphatic amines have the advantage of low toxicity and low viscosity, which enable them some processing advantages over other types of epoxy curatives for most applications. However, for PCB applications the high-reactivity of aliphatic amines with epoxy resin at ambient temperatures make them effectively unsuitable for the prepreg manufacturing process. The conventional aliphatic amines that are widely used in coatings and composite applications, like for example, polyethyleneamines, polyetheramines, and cycloaliphatic amines (e.g., isophorone diamine) have gel times ranging from minutes to hours at room temperature and do not possess sufficient latency. Further, conventional aliphatic amines do not readily form a B-stage with epoxy resins, for any suitable period. This general characteristic makes aliphatic amine molecules effectively unsuitable for standard prepreg manufacturing of PCB laminates. Another critical reason as to why aliphatic amines are not used in epoxy-based PCB applications is that aliphatic amine cured epoxies typically have decomposition temperatures, glass transition temperatures (Tg), DC, CTE, that are poorer than Aromatic amines-based, DICY-based, or anhydride-based hardeners systems. The diamino curing agents of as described by Formula (1) described herein overcome these limitations of conventional aliphatic amines used in the art in two major ways: 1) they are sterically hindered and therefore have low reactivity with epoxy resins at ambient temperatures; and 2) the contain an acid labile linkages, allowing a cured epoxy to be transformed (i.e. removed and recycled) by simple immersion in an acidic recycling bath.

As described herein, e.g., a compound of Formula (1) herein, a specific set of acid-labile and sterically hindered aliphatic amines is provided, which posses suitable processing, mechanical, thermal, and electrical properties, e.g., for PCB applications. These polyamine hardeners can be formulated to create epoxy composition suitable for the fabrication of laminates/prepregs that may serve as the structural materials for PCB applications. Furthermore, the curing agents provide an thermosetting epoxy matrix that enables the fabrication of inherently recyclable PCB laminate materials. The structure of the cross-links in the cured epoxy matrix from the epoxy compositions disclosed herein is designed in such a way that they are programmed to cleave upon immersion in an acidic recycling bath. The acidic bath induces cleavage of the acid-labile linkages in the thermoset, converting into its thermoplastic counterpart. Both the concentration of acid, and the acid strength (i.e. pH) of the recycling bath can be used to modulate the conversion of the reworkable thermoset into a thermoplastic. The nature of the acid-labile ketal/acetals group can be used as a handle to control the recycling time. Polymers modified with acid-cleavable groups have been successfully implemented in both photoresist and drug delivery applications. The common premise in these cases is that acid-induced cleavage will result in a solubility change in the parent material. This change is then taken advantage of for a technological purpose. The concept of recyclable/reworkable epoxy is somewhat similar, albeit the desired change is to transform an otherwise intractable material into a tractable one that is of high inherent value. The cleavage groups in the programmed epoxy hardeners will exist at every cross-link point in the cured epoxy matrix. Immersion of the cured epoxy in a specific recycling bath will induce cleavage of the cross-links and conversion of the thermoset plastic into its thermoplastic epoxy counterpart. This transformation occurs at an appreciable rate only upon immersion of the thermoset in a solution of sufficient temperature, acid strength and concentration. Generally, most epoxy and composite applications operate in environments that are far away from what is required to trigger the programmed epoxy to convert (e.g., degrade, de-crosslink). The thermoplastic offset is completely insoluble in water, but is solubilized into the acidic recycling solution because of protonation of the polymer backbone. Thus, any other articles in contact with the initial thermoset (fibers, metal, etc) may be physically removed from the recycling bath and then the dissolved epoxy thermoplastic recovered after a processing step such as evaporation or precipitation.

The exact conditions required (time, temperature, acid strength) to induce the conversion of the reworkable thermoset into a thermoplastic is governed by the exact chemical nature of the acid-labile group in the hardener. In general, the rate of acid hydrolysis is ketal>acetal>formal. For epoxy resins cured with the hardeners of Formula (1), the rate of dissolution of the cured epoxy is generally Hardener H-(1-1)>Hardener H-(1-3)>Hardener H-(1-2)>Hardener H-(1-4) >>Hardener H-(1-5). This trend is clearly seen via examination of the recycling half-life of the neat resins provided in Table 1.

In some embodiments, the fibers, metals, copper sheet, flame retardant additives, or any other articles on a PCB board that are insoluble in the acid batch, may be recovered by physical removal from the resultant/recycling solution. Further the dissolved epoxy thermoplastic may be recovered from the solution via a simple precipitation or evaporation process. An advantage of the described epoxy resin compositions and methods is that essentially all of the high value input materials of a PCB may be recovered via a simpler, and low energy recycling process, which is afforded by the use of Formula (1) cross-linking agents. Such a PCB recycling process may be performed at the site of product manufacturing, whereby prost-production PCB waste can be recycled instead of being thrown in the landfill. The described epoxy resin compositions and methods have important environmental and economic implications, as the development of a recyclable PCB materials is a long-standing challenge of the industry.

As described herein, novel polyamine hardener Formula (1) when used with a typical epoxy resin makes it possible to fabricate epoxy laminates for PCB applications, wherein the epoxy can be dissolved, separated and recovered. Among the embodiments of this invention is the incorporation of additional auxiliary material(s) to the base-epoxy composition (i.e., the "A-stage formulation"). The described epoxy resin compositions and methods have the distinct advantage that it enables the manufacture of recyclable printed circuit boards.

In an embodiment, the described epoxy resin compositions and methods have the distinct advantage that it provides epoxy compositions for the fabrication of more easily recycled PCBs. The described epoxy resin compositions and methods are not limited with respect to the exact method used, e.g., to make the laminate or prepreg that is used to make a final PCB product. A specific, but non-limiting example, of a procedure for forming prepregs and laminates for printed circuit boards involve such operations as:

A) An epoxy composition (e.g., formulation) is applied to or impregnated into a substrate by rolling, dipping, spraying, other known techniques and/or combinations thereof. The substrate can be an inorganic or organic reinforcing agent in the form of fibers, fleece, fabric or textile material (e.g., typically a woven or non-woven fiber mat containing, for example, glass fibers or paper).

B) The impregnated substrate is "B-staged" by heating at a temperature sufficient to draw off solvent in the composition (e.g., formulation) and optionally to partially cure the epoxy composition (e.g., formulation), so that the impregnated substrate is dry to the touch (i.e. "tack-free") and can be handled easily. The B-staging step is usually carried out with temperature of from 21° C. to 90° C. The impregnated substrate that results from B-Staging is commonly referred to as a "prepreg."

C) One or more sheets of prepreg are stacked or laid-up in alternating layers with one or more sheets of a conductive materials, such as copper foil, if an electrical laminate is desired.

D) The laid-up sheets are pressed at high temperature and pressure for a time sufficient to fully cure the epoxy composition and form a laminate. The temperature of this lamination step is usually between 100° C. and 230° C., and is most often between 165° C. and 190° C. The pressure is usually between 50 N/cm$^2$ and 500 N/cm$^2$. The lamination step is usually carried out for a time of from 1 minute to 200 minutes, and most often between 20 minutes to 90 minutes. The lamination step may optionally be carried out at higher temperatures for shorter times (such as in continuous lamination processes) or for longer times at lower temperatures (such as in low energy press processes).

E) Optionally, the resulting laminate, for example, a copper-clad laminate, may be post-treated for a time at high temperature and ambient pressure. The temperature of post-treatment is usually between 120° C. and 250° C. The post-treatment usually is between 30 minutes and 12 hours.

F) Often an electrically-conductive printed circuit is applied to the copper-clad laminate.

The blending ratio of the epoxy resin and the curing agent (e.g., an agent of Formula (1)) in the curable resin composition described herein is not particularly limited and can be selected to maximize the thermal, electrical, and physical properties of the final cured epoxy system. However from the standpoint that characteristics of the resulting cured product are good, the amount of active group in the Formula I is preferably 0.7 to 1.5 equivalents relative to the total 1 equivalent of the epoxy group of the epoxy resin.

Furthermore, in order to exhibit flame retardancy, for example in the field of printed writing board, the curable resin composition described herein may contain a halogenated flame retardant. There are a wide variety of brominated flame retardants that may be used in the epoxy composition. Some specific, but non-limiting examples, are those under the trade name Saytex®, GreenArmor® and GreenCrest from the Albemarle Corporation.

Furthermore, in order to exhibit flame retardancy, for example in the field of printed writing boards, the curable resin composition described herein may contain a non-halogenated flame retardant that substantially contains no halogen atoms within the range that does not degrade reliability. Specific, but non-limiting examples of non-halogenated flame-retardants include phosphorus-based flame retardants, inorganic flame retardants, silcone-based flame retardants, inorganic flame retardants, and organic metal salt-based flame retardants. The use of such flame retardants may be used alone or in a plurality.

As the phosphorus-based flame retardants, both inorganic compounds and organic compounds can be used. Examples of the inorganic compounds include red phosphorus; ammonium phosphates such as monoammonium phosphate, diammonium phosphate, triammonium phosphate, and ammonium polyphosphate; and inorganic nitrogen-containing phosphorus compounds such as phosphoric acid amide.

Red phosphorus is preferably subjected to a surface treatment in order to prevent hydrolysis or the like. Examples of the process of the surface treatment include (i) a process of coating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a process of coating with a mixture of an inorganic compound such as magnesium hydroxide, aluminum hydroxide, zinc hydroxide, or titanium hydroxide and a thermosetting resin such as a phenolic resin, and (iii) a process of coating with a film composed of an inorganic compound such as magnesium hydroxide, aluminum hydroxide, zinc hydroxide, or titanium hydroxide and further coating the inorganic compound film with a film composed of a thermosetting resin such as a phenolic resin.

Examples of the organic phosphorus-based compound include general-purpose organic phosphorus-based compounds such as phosphate ester compounds, phosphonic acid compounds, phosphinic acid compounds, phosphine oxide compounds, phosphorane compounds, and organic nitrogen-containing phosphorus compounds. Examples further include cyclic organic phosphorus compounds such as 9,10-dihydro-9-oxa-10-phosphaphenanthrene=10-oxide, 10-(2,5-dihydroxyphenyl)-10H-9-oxa-10-phosphaphenanthrene=10-oxide, and 10-(2,7-dihydroxynaphthyl)-10H-9-oxa-10-phosphaphenanthrene=10-oxide; and derivatives obtained by allowing any of these compounds react with a compound such as an epoxy resin or a phenolic resin.

The amount of the phosphorus-based flame retardant is appropriately selected in accordance with the type of phosphorus-based flame retardant, other components of the curable resin composition, and the degree of desired flame retardancy. For example, when red phosphorus is used as the non-halogen flame retardant in 100 parts by mass of a curable resin composition containing all components, such as an epoxy resin, a curing agent, a non-halogen flame retardant, and other fillers and additives, red phosphorus is preferably incorporated in an amount in the range of 0.1 to 2.0 parts by mass. When an organic phosphorous compound is used, similarly, the organic phosphorous compound is incorporated in an amount preferably in the range of 0.1 to 10.0 parts by mass, and particularly preferably in the range of 0.5 to 6.0 parts by mass.

When the phosphorous-based flame retardant is used, the phosphorous-based flame retardant may be used in combination with, for example, hydrotalcite, magnesium hydroxide, boron compounds, zirconium oxide, black dyes, calcium carbonate, zeolite, zinc molybdate, or activated carbon.

Examples of nitrogen-based flame retardants include triazine compounds, cyanuric acid compounds, isocyanuric acid compounds, and phenothiazine. In some embodiments, the nitrogen-based flame retardants are selected from triazine compounds, cyanuric acid compounds, or isocyanuric acid compounds.

Examples of triazine compounds include melamine, acetoguanamine, benzoguanamine, melon, melam, succinoguanamine, ethylenedimelamine, melamine polyphosphate, and triguanamine. Besides these compounds, examples thereof further include (i) aminotriazine sulfate compounds such as guanylmelamine sulfate, melem sulfate, and melam sulfate; (ii) co-condensates of a phenol such as phenol, cresol, xylenol, butylphenol, or nonylphenol, a melamine such as melamine, benzoguanamine, acetoguanamine, or formguanamine, and formaldehyde; (iii) mixtures of the cocondensate (ii) mentioned above and a phenolic resin such as a phenol-formaldehyde condensate; and (iv) those obtained by modifying the cocondensate (ii) or the mixture (iii) with, for example, tung oil or isomerized linseed oil.

Specific examples of the cyanuric acid compound include cyanuric acid and melamine cyanurate.

The amount of the nitrogen-based flame retardant is appropriately selected in accordance with the type of nitrogen-based flame retardant, other components of the curable resin composition, and the degree of desired flame retardancy. For example, the nitrogen-based flame retardant is preferably incorporated within the range of 0.05 to 10 parts by mass, and particularly preferably 0.1 to 5 parts by mass relative to 100 parts by mass of a curable resin composition containing all components, such as an epoxy resin, a curing agent, a non-halogen flame retardant, and other fillers and additives.

When the nitrogen-based flame retardant is used, for example, a metal hydroxide or a molybdenum compound may be used in combination.

The silicone-based flame retardants are not particularly limited so long as the flame retardant is an organic compound having a silicon atom. Examples thereof include silicone oil, silicone rubber, and silicone resins.

The amount of the silicone-based flame retardant is appropriately selected in accordance with the type of silicone-based flame retardant, other components of the curable resin composition, and the degree of desired flame retardancy. For example, the silicone-based flame retardant is preferably incorporated within the range of 0.05 to 20 parts by mass relative to 100 parts by mass of a curable resin composition containing all components, such as an epoxy resin, a curing agent, a non-halogen flame retardant, and other fillers and additives. When the silicone-based flame retardant is used, for example, a molybdenum compound or alumina may be used in combination.

Examples of the inorganic flame retardant include metal hydroxides, metal oxides, metal carbonate compounds, metal powders, boron compounds, and low-melting-point glass.

Specific examples of the metal hydroxide include aluminum hydroxide, magnesium hydroxide, dolomite, hydrotalcite, calcium hydroxide, barium hydroxide, and zirconium hydroxide.

Specific examples of the metal oxide include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Specific examples of the metal carbonate compound include zinc carbonate, magnesium carbonate, calcium carbonate, barium carbonate, basic magnesium carbonate, aluminum carbonate, iron carbonate, cobalt carbonate, and titanium carbonate.

Specific examples of the metal powder include powders of aluminum, iron, titanium, manganese, zinc, molybdenum, cobalt, bismuth, chromium, nickel, copper, tungsten, and tin.

Specific examples of the boron compound include zinc borate, zinc metaborate, barium metaborate, boric acid, and borax.

Specific examples of the low-melting-point glass include Seaplea (Bokusui Brown Co., Ltd.), hydrated glass $SiO_2$—$MgO$—$H_2O$, $PbO$—$B_2O_3$-based, $ZnO$—$P_2O_5$—$MgO$-based, $P_2O_5$—$B_2O_3$—$PbO$—$MgO$-based, P—Sn—O—F-based, $PbO$—$V_2O_5$—$TeO_2$-based, $Al_2O_3$—$H_2O$-based, and lead borosilicate-based glassy compounds.

The amount of the inorganic flame retardant is appropriately selected in accordance with the type of inorganic flame retardant, other components of the curable resin composition, and the degree of desired flame retardancy. For example, the inorganic flame retardant is preferably incorporated within the range of 0.05 to 20 parts by mass, and particularly preferably from 0.5 to 15 parts by mass relative to 100 parts by mass of a curable resin composition containing all components, such as an epoxy resin, a curing agent, a non-halogen flame retardant, and other fillers and additives.

Examples of the organic metal salt-based flame retardant include ferrocene, acetylacetonate metal complexes, organometallic carbonyl compounds, organic cobalt salt compounds, organic sulfonic acid metal salts, and compounds obtained by ionic bonding or coordinate bonding of a metal atom and an aromatic compound or a heterocyclic compound.

The amount of the organic metal salt-based flame retardant is appropriately selected in accordance with the type of organic metal salt-based flame retardant, other components of the curable resin composition, and the degree of desired flame retardancy. For example, the organic metal salt-based flame retardant is preferably incorporated within the range of 0.005 to 10 parts by mass relative to 100 parts by mass of a curable resin composition containing all components, such as an epoxy resin, a curing agent, a non-halogen flame retardant, and other fillers and additives.

The curable resin composition described herein may contain inorganic fillers, if necessary. Examples of the inorganic filler include fused silica, crystalline silica, alumina, silicon nitride, and aluminum hydroxide. When the amount of the inorganic filler is particularly large, fused silica is preferably used. The fused silica can be used in a crushed or spherical form, but it is preferable to mainly use spherical fused silica in order to increase the amount of fused silica blended and to suppress an increase in the melt viscosity of the resulting molding material. In order to further increase the amount of spherical silica blended, it is preferable to appropriately adjust particle size distribution of the spherical silica. In consideration of flame retardancy, the filling ratio of the filler is preferably high and is particularly preferably 20% by mass or more of the total amount of the curable resin composition. When the curable resin composition is used in the application of an electrically conductive paste or the like, an electrically conductive filler such as a silver powder or a copper powder can be used.

Various compounding agents such as a silane coupling agent, a mold release agent, a pigment, and an emulsifier may be optionally added to the curable resin composition described herein.

In some embodiments, epoxy resin composition described herein further includes a reinforcing agent. In one embodiment, reinforcing agent is selected from a group consisting of glass fiber, carbon fiber, natural fiber, and chemical fiber; and the non-fibrous material is at least one selected from a group consisting of carbon nanotube, carbon black, metal nanoparticle, organic nanoparticle, iron oxide, boron nitride, and combinations thereof.

In another aspect, described herein is a method of curing an epoxy resin composition described herein. In one embodiment, the method comprises heating an epoxy resin composition described herein to form a cured epoxy resin composition. In one embodiment, the epoxy resin composition is cured to a curing degree of at least 5% cure (e.g., as determined by infrared (IR) spectroscopy, differential scanning calorimetry (DSC), or other methods used by a person of skill in the art. In one embodiment, the epoxy resin composition is cured to a curing degree of at least 10% cure. In one embodiment, the epoxy resin composition is cured to a curing degree of at least 15% cure. In one embodiment, the epoxy resin composition is cured to a curing degree of at least 20% cure. In one embodiment, the epoxy resin composition is cured to a curing degree of at least 25% cure. In one embodiment, the epoxy resin composition is cured to a curing degree of at least 30% cure. In one embodiment, the epoxy resin composition is cured to a curing degree of at least 35% cure. In one embodiment, the epoxy resin composition is cured to a curing degree of at least 45% cure. In one embodiment, the epoxy resin composition is cured to a curing degree of at least 55% cure. In one embodiment, the epoxy resin composition is cured to a curing degree selected from the group consisting of at least 65% cure, at least 75% cure, at least 85% cure, and at least 95% cure.

In some embodiments, the method of curing an epoxy resin composition described herein is used to produce reinforced composite. In one embodiment, the method of curing an epoxy resin composition described herein produces a composite reinforced with a reinforcing component selected from the group consisting of glass fibers, aramid fibers, graphite fibers, carbon fibers, natural fibers, non-natural fibers and combinations thereof.

In one embodiment, the cross-linked polymer matrix is reinforced with a reinforcing agent derived from a reinforcing component selected from the group consisting of glass fibers, aramid fibers, graphite fibers, carbon fibers, natural fibers, non-natural fibers and combinations thereof. In one embodiment, the cross-linked polymer matrix is a cross-linked epoxy resin, wherein the epoxy resin is selected from the group consisting of glycidyl ether epoxy resin, glycidyl ester epoxy resin, glycidyl amine epoxy resin, alicyclic epoxy resin, aliphatic epoxy resin, and phenolic epoxy resin. In one embodiment, the cross-linked polymer matrix is reinforced with the reinforcement material selected from the group consisting of a fibrous material and a non-fibrous material. In one embodiment, the cross-linked polymer matrix is reinforced with a fibrous material selected from a group consisting of glass fiber, carbon fiber, natural fiber, and chemical fiber. In one embodiment, the cross-linked polymer matrix is reinforced with a non-fibrous material selected from the group consisting of carbon nanotube, carbon black, metal nanoparticle, organic nanoparticle, iron oxide, and boron nitride. In one embodiment, the reinforced cross-linked polymer matrix includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, and gloss additive. In some embodiments, the reinforced cross-linked polymer matrix is prepared by at least one method selected from the group consisting of wet lay-up, vacuum infusion, filament winding, and resin transfer molding, prepreg, and compression molding.

In another aspect, described herein is a method for recycling a cross-linked polymer matrix described herein. FIG. 1 shows a non-limiting example of the method for recycling a cross-linked polymer matrix described herein. In one embodiment, the method for recycling the cross-linked polymer matrix comprises degrading the cross-linked polymer matrix with an acid in the presence of a solvent. In one embodiment, degrading the cross-linked matrix with an acid in the presence of a solvent is performed under a heating condition. In one embodiment, the cross-linked polymer matrix is degraded with an acid selected from a group consisting of hydrochloric acid, acetic acid, lactic acid, formic acid, propionic acid, citric acid, methane sulfonic acid, p-toluene sulfonic acid, sulfuric acid, benzoic acid, and phthalic acid. In one embodiment, the cross-linked polymer matrix is degraded with an acid in the presence of a solvent selected from the group consisting of methanol, ethanol, ethylene glycol, isopropyl alcohol, butyl alcohol, pentanol, hexanol, heptanol, octanol alcohol, nonyl alcohol, water, and combinations thereof. In one embodiment, the cross-linked polymer matrix is degraded with an acid in an amount ranging from about 2% to 90% by weight of the cross-linked polymer matrix. In one embodiment, the cross-linked polymer matrix is degrated with an acid in an amount selected from about 2 wt. % to about 90 wt. %, about 3 wt. % to about 90 wt. %, about 4 wt. % to about 90 wt. %, about 5 wt. % to about 90 wt. %, about 6 wt. % to about 90 wt. %, about 7 wt. % to about 90 wt. %, about 8 wt. % to about 90 wt. %, about 9 wt. % to about 90 wt. %, about 10 wt. % to about 90 wt. %, about 11 wt. % to about 90 wt. %, about 12 wt. % to about 90 wt. %, about 13 wt. % to about 90 wt. %, about 14 wt. % to about 90 wt. %, about 15 wt. % to about 90 wt. %, about 16 wt. % to about 90 wt. %, about 17 wt. % to about 90 wt. %, about 18 wt. % to about 90 wt. %, about 19 wt. % to about 90 wt. %, about 20 wt. % to about 90 wt. %, about 21 wt. % to about 90 wt. %, about 22 wt. % to about 90 wt. %, about 23 wt. % to about 90 wt. %, about 24 wt. % to about 90 wt. %, about 25 wt. % to about 90 wt. %, about 26 wt. % to about 90 wt. %, about 27 wt. % to about 90 wt. %, about 28 wt. % to about 90 wt. %, about 29 wt. % to about 90 wt. %, about 30 wt. % to about 90 wt. %, about 31 wt. % to about 90 wt. %, about 32 wt. % to about 90 wt. %, about 33 wt. % to about 90 wt. %, about 34 wt. % to about 90 wt. %, about 35 wt. % to about 90 wt. %, about 36 wt. % to about 90 wt. %, about 37 wt. % to about 90 wt. %, about 38 wt. % to about 90 wt. %, about 39 wt. % to about 90 wt. %, about 40 wt. % to about 90 wt. %, about 41 wt. % to about 90 wt. %, about 42 wt. % to about 90 wt. %, about 43 wt. % to about 90 wt. %, about 44 wt. % to about 90 wt. %, about 45 wt. % to about 90 wt. %, about 46 wt. % to about 90 wt. %, about 47 wt. % to about 90 wt. %, about 48 wt. % to about 90 wt. %, about 49 wt. % to about 90 wt. %, about 50 wt. % to about 90 wt. %, about 51 wt. % to about 90 wt. %, about 52 wt. % to about 90 wt. %, about 53 wt. % to about 90 wt. %, about 54 wt. % to about 90 wt. %, about 55 wt. % to about 90 wt. %, about 56 wt. % to about 90 wt. %, about 57 wt. % to about 90 wt. %, about 58 wt. % to about 90 wt. %, about 59 wt. % to about 90 wt. %, about 60 wt. % to about 90 wt. %, about 61 wt. % to about 90 wt. %, about 62 wt. % to about 90 wt. %, about 63 wt. % to about 90 wt. %, about 64 wt. % to about 90 wt. %, about 65 wt. % to about 90 wt. %, about 66 wt. % to about 90 wt. %, about 67 wt. % to about 90 wt. %, about 68 wt. % to about 90 wt. %, about 69 wt. % to about 90 wt. %, about 70 wt. % to about 90 wt. %, about 71 wt. % to about 90 wt. %, about 72 wt. % to about 90 wt. %, about 73 wt. % to about 90 wt. %, about 74 wt. % to about 90 wt. %, about 75 wt. % to about 90 wt. %, about 76 wt. % to about 90 wt. %, about 77 wt. % to about 90 wt. %, about 78 wt. % to about 90 wt. %, about 79 wt. % to about 90 wt. %, about 80 wt. % to about 90 wt. %, about 81 wt. % to about 90 wt. %, about 82 wt. % to about 90 wt. %, about 83 wt. % to about 90 wt. %, about 84 wt. % to about 90 wt. %, about 85 wt. % to about 90 wt. %, about 86 wt. % to about 90 wt. %, about 87 wt. % to about 90 wt. %, about 88 wt. % to about 90 wt. %, and about 89 wt. % to about 90 wt. % of the cross-linked polymer matrix.

In one embodiment, the cross-linked polymer matrix is degraded with an acid in an amount selected from the group consisting of about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, and about 90 wt. % of the polymer matrix.

In some embodiments, the method for recycling a cross-linked polymer matrix described herein is carried out under a heating condition. In one embodiment, the cross-linked polymer matrix is degraded at a temperature ranging from 15° C. to 400° C. In one embodiment, the cross-linked polymer matrix is degraded at a temperature ranging from 60° C. to 120° C. In one embodiment, the cross-linked polymer matrix is degraded at a temperature selected from the group consisting of about 60° C. to about 120° C., about 61° C. to about 120° C., about 62° C. to about 120° C., about 63° C. to about 120° C., about 64° C. to about 120° C., about 65° C. to about 120° C., about 66° C. to about 120° C., about 67° C. to about 120° C., about 68° C. to about 120° C., about 69° C. to about 120° C., about 70° C. to about 120° C., about 71° C. to about 120° C., about 72° C. to about 120° C., about 73° C. to about 120° C., about 74° C. to about 120° C., about 75° C. to about 120° C., about 76° C. to about 120° C., about 77° C. to about 120° C., about 78° C. to about 120° C., about 79° C. to about 120° C., about 80° C. to about 120° C., about 81° C. to about 120° C., about 82° C. to about 120° C., about 83° C. to about 120° C., about 84° C. to about 120° C., about 85° C. to about 120° C., about 86° C. to about 120° C., about 87° C. to about 120° C., about 88° C. to about 120° C., about 89° C. to about 120° C., about 90° C. to about 120° C., about 91° C. to about 120° C., about 92° C. to about 120° C., about 93° C. to about 120° C., about 94° C. to about 120° C., about 95° C. to about 120° C., about 96° C. to about 120° C., about 97° C. to about 120° C., about 98° C. to about 120° C., about 99° C. to about 120° C., about 100° C. to about 120° C., about 101° C. to about 120° C., about 102° C. to about 120° C., about 103° C. to about 120° C., about 104° C. to about 120° C., about 105° C. to about 120° C., about 106° C. to about 120° C., about 107° C. to about 120° C., about 108° C. to about 120° C., about 109° C. to about 120° C., about 110° C. to about 120° C., about 111° C. to about 120° C., about 112° C. to about 120° C., about 113° C. to about 120° C., about 114° C. to about 120° C., about 115° C. to about 120° C., about 116° C. to about 120° C., about 117° C. to about 120° C., about 118° C. to about 120° C., and about 119° C. to about 120° C.

In one embodiment, the cross-linked polymer matrix is degraded at a temperature selected from the group consisting of about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C., about 116° C., about 117° C., about 118° C., about 119° C., and about 120° C.

In some embodiments, the cross-linked polymer matrix is degraded at a temperature ranging from 20° C. to 400° C. In one embodiment, the cross-linked polymer matrix is degraded at a temperature selected from the group consisting of about 20° C. to about 400° C., about 25° C. to about 400° C., about 30° C. to about 400° C., about 35° C. to about 400° C., about 40° C. to about 400° C., about 45° C. to about 400° C., about 50° C. to about 400° C., about 55° C. to about 400° C., about 60° C. to about 400° C., about 65° C. to about 400° C., about 70° C. to about 400° C., about 75° C. to about 400° C., about 80° C. to about 400° C., about 85° C. to about 400° C., about 90° C. to about 400° C., about 95° C. to about 400° C., about 100° C. to about 400° C., about 105° C. to about 400° C., about 110° C. to about 400° C., about 115° C. to about 400° C., about 120° C. to about 400° C., about 125° C. to about 400° C., about 130° C. to about 400° C., about 135° C. to about 400° C., about 140° C. to about 400° C., about 145° C. to about 400° C., about 150° C. to about 400° C., about 155° C. to about 400° C., about 160° C. to about 400° C., about 165° C. to about 400° C., about 170° C. to about 400° C., about 175° C. to about 400° C., about 180° C. to about 400° C., about 185° C. to about 400° C., about 190° C. to about 400° C., about 195° C. to about 400° C., about 200° C. to about 400° C., about 205° C. to about 400° C., about 210° C. to about 400° C., about 215° C. to about 400° C., about 220° C. to about 400° C., about 225° C. to about 400° C., about 230° C. to about 400° C., about 235° C. to about 400° C., about 240° C. to about 400° C., about 245° C. to about 400° C., about 250° C. to about 400° C., about 255° C. to about 400° C., about 260° C. to about 400° C., about 265° C. to about 400° C., about 270° C. to about 400° C., about 275° C. to about 400° C., about 280° C. to about 400° C., about 285° C. to about 400° C., about 290° C. to about 400° C., about 295° C. to about 400° C., about 300° C. to about 400° C., about 305° C. to about 400° C., about 310° C. to about 400° C., about 315° C. to about 400° C., about 320° C. to about 400° C., about 325° C. to about 400° C., about 330° C. to about 400° C., about 335° C. to about 400° C., about 340° C. to about 400° C., about 345° C. to about 400° C., about 350° C. to about 400° C., about 355° C. to about 400° C., about 360° C. to about 400° C., about 365° C. to about 400° C., about 370° C. to about 400° C., about 375° C. to about 400° C., about 380° C. to about 400° C., about 385° C. to about 400° C., about 390° C. to about 400° C., and about 395° C. to about 400° C.

In some embodiments, the cross-linked polymer matrix is degraded at a temperature selected from the group consisting of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 215° C., about 220° C., about 225° C., about 230° C., about 235° C., about 240° C., about 245° C., about 250° C., about 255° C., about 260° C., about 265° C., about 270° C., about 275° C., about 280° C., about 285° C., about 290° C., about 295° C., about 300° C., about 305° C., about 310° C., about 315° C., about 320° C., about 325° C., about 330° C., about 335° C., about 340° C., about 345° C., about 350° C., about 355° C., about 360° C., about 365° C., about 370° C., about 375° C., about 380° C., about 385° C., about 390° C., about 395° C., and about 400° C.

In some embodiments, the cross-linked polymer matrix is degraded by heating the cross-linked polymer matrix with an acid at a temperature selected from the group consisting of less than about 400° C. but greater than about 10° C., less than about 395° C. but greater than about 10° C., less than about 390° C. but greater than about 10° C., less than about 385° C. but greater than about 10° C., less than about 380° C. but greater than about 10° C., less than about 375° C. but greater than about 10° C., less than about 370° C. but greater than about 10° C., less than about 365° C. but greater than about 10° C., less than about 360° C. but greater than about 10° C., less than about 355° C. but greater than about 10° C., less than about 350° C. but greater than about 10° C., less than about 345° C. but greater than about 10° C., less than about 340° C. but greater than about 10° C., less than about 335° C. but greater than about 10° C., less than about 330° C. but greater than about 10° C., less than about 325° C. but greater than about 10° C., less than about 320° C. but greater than about 10° C., less than about 315° C. but greater than about 10° C., less than about 32° C. but greater than about 10° C., less than about 305° C. but greater than about 10° C., less than about 300° C. but greater than about 10° C., less than about 295° C. but greater than about 10° C., less than about 290° C. but greater than about 10° C., less than about 285° C. but greater than about 10° C., less than about 280° C. but greater than about 10° C., less than about 275° C. but greater than about 10° C., less than about 270° C. but greater than about 10° C., less than about 265° C. but greater than about 10° C., less than about 260° C. but greater than about 10° C., less than about 255° C. but greater than about 10° C., less than about 250° C. but greater than about 10° C., less than about 245° C. but greater than about 10° C., less than about 240° C. but greater than about 10° C., less than about 235° C. but greater than about 10° C., less than about 230° C. but greater than about 10° C., less than about 225° C. but greater than about 10° C., less than about 220° C. but greater than about 10° C., less than about 215° C. but greater than about 10° C., less than about 22° C. but greater than about 10° C., less than about 205° C. but greater than about 10° C., less than about 200° C. but greater than about 10° C., less than about 195° C. but greater than about 10° C., less than about 190° C. but greater than about 10° C., less than about 185° C. but greater than about 10° C., less than about 180° C. but greater than about 10° C., less than about 175° C. but greater than about 10° C., less than about 170° C. but greater than about 10° C., less than about 165° C. but greater than about 10° C., less than about 160° C. but greater than about 10° C., less than about 155° C. but greater than about 10° C., less than about 150° C. but greater than about 10° C., less than about 145° C. but greater than about 10° C., less than about 140° C. but greater than about 10° C., less than about 135° C. but greater than about 10° C., less than about 130° C. but greater than about 10° C., less than about 125° C. but greater than about 10° C., less than about 120° C. but greater than about 10° C., less than about 115° C. but greater than about 10° C., less than about 12° C. but greater than about 10° C., less than about 105° C. but greater than about 10° C., less than about 100° C. but greater than about 10° C., less than about 95° C. but greater than about 10° C., less than about 90° C. but greater than about 10° C., less than about 85° C. but greater than about 10° C., less than about 80° C. but greater than about 10° C., less than about 75° C. but greater than about 10° C., less than about 70° C. but greater than about 10° C., less than about 65° C. but greater than about 10° C., less than about 60° C. but greater than about 10° C., less than about 55° C. but greater than about 10° C., less than about 50° C. but greater than about 10° C., less than about 45° C. but greater than about 10° C., less than about 40° C. but greater than about 10° C., less than about 35° C. but greater than about 10° C., less than about 30° C. but greater than about 10° C., less than about 25° C. but greater than about 10° C., less than about 20° C. but greater than about 10° C., and less than about 15° C. but greater than about 10° C.

In some embodiments, the cross-linked polymer matrix is degraded by heating the cross-linked polymer matrix with an acid for a time of from about 1 hour to about 48 hours. In some embodiments, the cross-linked polymer matrix is degraded by heating the cross-linked polymer matrix with an acid for a time of from about 1 hour to 12 hours.

In some embodiments, the cross-linked polymer matrix is degraded by heating the cross-linked polymer matrix with an acid for a time selected from the group consisting of about 1 hour to about 48 hours, about 2 hours to about 48 hours, about 3 hours to about 48 hours, about 4 hours to about 48 hours, about 5 hours to about 48 hours, about 6 hours to about 48 hours, about 7 hours to about 48 hours, about 8 hours to about 48 hours, about 9 hours to about 48 hours, about 10 hours to about 48 hours, about 11 hours to about 48 hours, about 12 hours to about 48 hours, about 13 hours to about 48 hours, about 14 hours to about 48 hours, about 15 hours to about 48 hours, about 16 hours to about 48 hours, about 17 hours to about 48 hours, about 18 hours to about 48 hours, about 19 hours to about 48 hours, about 20 hours to about 48 hours, about 21 hours to about 48 hours, about 22 hours to about 48 hours, about 23 hours to about 48 hours, about 24 hours to about 48 hours, about 25 hours to about 48 hours, about 26 hours to about 48 hours, about 27 hours to about 48 hours, about 28 hours to about 48 hours, about 29 hours to about 48 hours, about 30 hours to about 48 hours, about 31 hours to about 48 hours, about 32 hours to about 48 hours, about 33 hours to about 48 hours, about 34 hours to about 48 hours, about 35 hours to about 48 hours, about 36 hours to about 48 hours, about 37 hours to about 48 hours, about 38 hours to about 48 hours, about 39 hours to about 48 hours, about 40 hours to about 48 hours, about 41 hours to about 48 hours, about 42 hours to about 48 hours, about 43 hours to about 48 hours, about 44 hours to about 48 hours, about 45 hours to about 48 hours, about 46 hours to about 48 hours, and about 47 hours to about 48 hours.

In some embodiments, the cross-linked polymer matrix is degraded by heating the cross-linked polymer matrix with an acid for a time selected from the group consisting of less than about 48 hours but greater than about 1 hour, less than about 47 hours but greater than about 1 hour, less than about 46 hours but greater than about 1 hour, less than about 45 hours but greater than about 1 hour, less than about 44 hours but greater than about 1 hour, less than about 43 hours but greater than about 1 hour, less than about 42 hours but greater than about 1 hour, less than about 41 hours but greater than about 1 hour, less than about 40 hours but greater than about 1 hour, less than about 39 hours but greater than about 1 hour, less than about 38 hours but greater than about 1 hour, less than about 37 hours but greater than about 1 hour, less than about 36 hours but greater than about 1 hour, less than about 35 hours but greater than about 1 hour, less than about 34 hours but greater than about 1 hour, less than about 33 hours but greater than about 1 hour, less than about 32 hours but greater than about 1 hour, less than about 31 hours but greater than about 1 hour, less than about 30 hours but greater than about 1 hour, less than about 29 hours but greater than about 1 hour, less than about 28 hours but greater than about 1 hour, less than about 27 hours but greater than about 1 hour, less than about 26 hours but greater than about 1 hour, less than about 25 hours but greater than about 1 hour, less than about 24 hours but greater than about 1 hour, less than about 23 hours but greater than about 1 hour, less than about 22 hours but greater than about 1 hour, less than about 21 hours but greater than about 1 hour, less than about 20 hours but greater than about 1 hour, less than about 19 hours but greater than about 1 hour, less than about 18 hours but greater than about 1 hour, less than about 17 hours but greater than about 1 hour, less than about 16 hours but greater than about 1 hour, less than about 15 hours but greater than about 1 hour, less than about 14 hours but greater than about 1 hour, less than about 13 hours but greater than about 1 hour, less than about 12 hours but greater than about 1 hour, less than about 11 hours but greater than about 1 hour, less than about 10 hours but greater than about 1 hour, less than about 9 hours but greater than about 1 hour, less than about 8 hours but greater than about 1 hour, less than about 7 hours but greater than about 1 hour, less than about 6 hours but greater than about 1 hour, less than about 5 hours but greater than about 1 hour, less than about 4 hours but greater than about 1 hour, less than about 3 hours but greater than about 1 hour, and less than about 2 hours but greater than about 1 hour.

In some embodiments, the cross-linked polymer matrix is degraded by heating the cross-linked polymer matrix with an acid for a time selected from the group consisting of 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, and about 48 hours.

In some embodiments, the cross-linked polymer matrix is degraded by heating the cross-linked polymer matrix with an acid for a time selected from the group consisting of less than about 48 hours but greater than about 1 hour, less than about 47 hours but greater than about 2 hours, less than about 46 hours but greater than about 3 hours, less than about 45 hours but greater than about 4 hours, less than about 44 hours but greater than about 5 hours, less than about 43 hours but greater than about 6 hours, less than about 42 hours but greater than about 7 hours, less than about 41 hours but greater than about 8 hours, less than about 40 hours but greater than about 9 hours, less than about 39 hours but greater than about 10 hours, less than about 38 hours but greater than about 11 hours, less than about 37 hours but greater than about 12 hours, less than about 36 hours but greater than about 13 hours, less than about 35 hours but greater than about 14 hours, less than about 34 hours but greater than about 15 hours, less than about 33 hours but greater than about 16 hours, less than about 32 hours but greater than about 17 hours, less than about 31 hours but greater than about 18 hours, less than about 30 hours but greater than about 19 hours, less than about 29 hours but greater than about 20 hours, less than about 28 hours but greater than about 21 hours, less than about 27 hours but greater than about 22 hours, less than about 26 hours but greater than about 23 hours, and less than about 25 hours but greater than about 24 hours.

In some embodiments, the method for recycling a cross-linked polymer matrix includes the step of recovering a degradation product of the cross-linked polymer matrix via a filtration process and/or a precipitation process.

In general, the diamino compounds of Formula (1) can be used as monomers and/or cross-linkers to make polymeric materials such as nylons, epoxies, polyurethanes, acrylamides or other type polymers or cross-linked polymers and/or materials. The diamino compounds of Formula (1) can also be used as monomers or cross-linkers for the preparation of designer materials that can further be imbued with the ability to degrade under acidic conditions. Polymer degradation can be accomplished with these materials because, inter alia, the incorporated acetal and ketal linkages are susceptible to cleavage by various chemical means. For example, the acetal and ketal linkages can be cleaved by hydrolysis under acidic conditions. Thus, use of the present diaminoacetals and diaminoketals of Formula (1) as monomers produce polymeric structure that can be predictably degraded into smaller molecular fragments under acidic conditions.

Similarly, use of the present diaminoacetals and diaminoketals of Formula (1) as cross-linkers produce polymeric materials that can be cleaved into smaller molecular fragments by cleaving the aminoacetal and aminoketals of the cross-links, for example, under acidic conditions. The rate of acid hydrolysis of acetal and ketals linkages can be used to fine-tune the physical properties of the polymeric materials. In general, the rate of acid hydrolysis decreases in the order of ketal>acetal>formal. Thus, polymeric materials that contain these acid-labile linkages can be useful in designing more environmentally sustainable materials that can be degraded at will via chemical means.

In some embodiments, the epoxy resin composition disclosed herein can be used as an adhesive composition. In some embodiments, the epoxy composition disclosed herein can be used as a coating composition. In some embodiments, the epoxy composition disclosed herein can be used as an encapsulation material.

The present disclosure details sterically hindered, cleavable polyamino compounds that provide epoxy resin compositions with extended working times and/or out-life that are suitable for use in industrial composite manufacturing techniques such as filament winding, pultrusion, prepreg, which are process that are otherwise not applicable to epoxy compositions that contain aliphatic polyamines. The epoxy resin compositions described herein may be used in oil and gas-related applications, e.g., for Cured In Place Pipe Repair (CIPP). Additionally, the epoxy compositions described herein have the ability to be easily removed, recycled, dissolved, or otherwise reworked after they have been cured. In an embodiment, a fluid can pass through an industrial composite comprising the epoxy composition described herein. In an embodiment, a first, non-dissolving (e.g., non-acidic) fluid is passed through the industrial composite comprising the epoxy composition described herein. In an embodiment, a second, dissolving (e.g., acidic) fluid is pass through the industrial composite comprising the epoxy composition described herein (e.g., to dissolve or degrade the epoxy composition described herein). The epoxy compositions described herein can also not be recycled or reworked. Thus, the described epoxy resin compositions and methods should find industrial application that include, as non-limiting examples, removable coatings and encapsulates, recyclable carbon fiber thermoset composites, recyclable fiberglass thermoset composites. An example of an industrial application for the epoxy compositions described herein include repair of e.g., an underground pipe, e.g., by layering a fiberglass sleeve in the resin. In some embodiments, the epoxy resin composition has enhanced pliability (due to its steric hindrance). An epoxy resin composition for CIPP is a specific, but non-limiting, example of an application.

It will be appreciated by those skilled in the art that changes could be made to the exemplary embodiments shown and described above without departing from the broad inventive concept thereof. It is understood, therefore, that the described epoxy resin compositions and methods are not limited to the exemplary embodiments shown and described, but it is intended to cover modifications within the spirit and scope of the disclosure and as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the methods described herein should not be limited to the performance of their steps in the order written, and one skilled in the art can readily appreciate that the steps may be varied and still remain within the spirit and scope of the present invention.

Definitions

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Aliphatic" refers to an alkyl, alkenyl, alkynyl, or carbocyclyl group, as defined herein.

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH═CH—) and propenylene (e.g., —CH═CHCH₂—, —CH₂—CH═CH—). Exemplary substituted alkenylene groups, e.g., substituted with one or more alkyl (methyl) groups, include but are not limited to, substituted ethylene (—C(CH₃)═CH—, —CH═C(CH₃)—), substituted propylene (e.g., —C(CH₃)═CHCH₂—, —CH═C(CH₃)CH₂—, —CH═CHCH(CH₃)—, —CH═CHC(CH₃)₂—, —CH(CH₃)—CH═CH—, —C(CH₃)₂—CH═CH—, —CH₂—C(CH₃)═CH—, —CH₂—CH═C(CH₃)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "aromatic" as employed herein refers to a polyunsaturated, aromatic or heteroaromatic moiety which can be a single ring or multiple rings (e.g., 1 to 2 rings), which are fused together or linked covalently. For example, an aromatic group can have from six to twelve carbon atoms (i.e., $C_6$-$C_{12}$ aromatic). Non-limiting examples of aromatic groups include phenyl, 1-naphthyl, 2-naphthyl, and 4-biphenyl.

Alkyl, cycloalkyl, and aromatic groups as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

I claim:

1. An epoxy resin composition comprising:
an epoxy resin; and
an aliphatic polyamine, wherein the aliphatic polyamine comprises a compound having the structure of Formula (1):

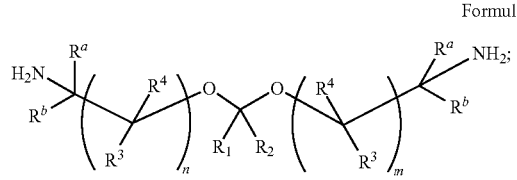

Formula (1)

wherein:
each of $R^1$ and $R^2$ is independently selected from the group consisting of hydrogen, alkyl group, cycloalkyl group and aromatic group; or
$R^1$ and $R^2$ together with the carbon atom to which they are attached form a cyclic ring;
each of $R^3$ and $R^4$ is independently selected from the group consisting of hydrogen, alkyl group, cycloalkyl group and aromatic group; or
$R^3$ and $R^4$ together with the carbon atom to which they are attached form a cyclic ring;
each $R^a$ and $R^b$ is independently selected from the group consisting of alkyl group, cycloalkyl group and aromatic group; and
each m and n is independently an integer ranging from 0 to 20; and
wherein the epoxy resin composition has working time of at least 5 hours.

2. The epoxy resin composition of claim 1, wherein the aliphatic polyamine is a sterically hindered aliphatic polyamine.

3. The epoxy resin composition of claim 2, wherein the sterically hindered aliphatic polyamine is of Formula (1-1):

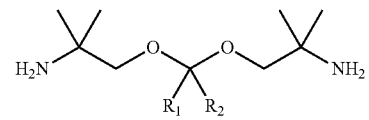

Formula (1-1)

wherein each of $R^1$ and $R^2$ is independently selected from the group consisting of hydrogen, alkyl group, cycloalkyl group and aromatic group; or
$R^1$ and $R^2$ together with the carbon atom to which they are attached form a cyclic ring.

4. The epoxy resin composition of claim 3, wherein each of $R^1$ and $R^2$ is independently selected from the group consisting of hydrogen, alkyl group, cycloalkyl group and aromatic group.

5. The epoxy resin composition of claim 3, wherein $R^1$ and $R^2$ together with the carbon atom to which they are attached form a cyclic ring.

6. The epoxy resin composition of claim 3, wherein the aliphatic polyamine is selected from the group consisting of:

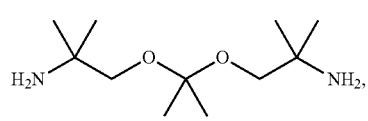

H-(1-1)

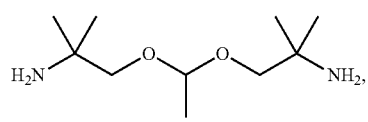

H-(1-2)

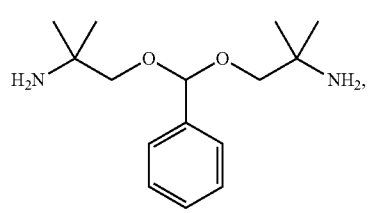

H-(1-3)

-continued

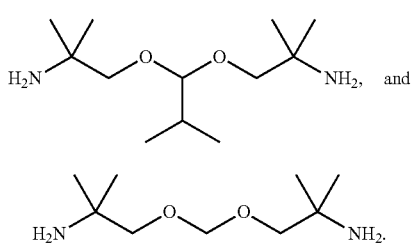

H-(1-4)

H-(1-5)

7. The epoxy resin composition of claim 6, wherein the aliphatic polyamine is:

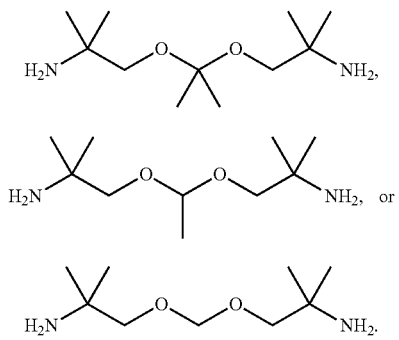

H-(1-1)

H-(1-2)

H-(1-5)

8. The epoxy resin composition of claim 1, wherein the epoxy resin comprises an average of at least two epoxide groups per molecule, i.e. at least two epoxide groups per monomer of the epoxy resin.

9. The epoxy resin composition of claim 1, wherein the epoxy resin comprises a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin and combinations thereof.

10. The epoxy resin composition of claim 1, wherein the epoxy resin comprises bisphenol A diglycidyl ether, bisphenol F diglycidyl ether, or oligomers thereof.

11. The epoxy resin composition of claim 1, wherein the epoxy resin comprises a mixture of a diglycidyl ether of a bisphenol having an EEW in the range of 150-195 and a diglycidyl ether of a bisphenol having an EEW in the range of 400 to 1500.

12. The epoxy resin composition of claim 1, further including an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, gloss additive, and combinations thereof.

13. The epoxy resin composition of claim 1, comprising an additional amino molecule.

14. The epoxy resin composition of claim 13, wherein the amino molecule comprises >2 N—H hydrogens.

15. The epoxy resin composition of claim 1, further including an amino molecule containing ≤2 N—H hydrogens.

16. The epoxy resin composition of claim 15, wherein the amino molecule containing ≤2 N—H hydrogens is selected from the group consisting of a primary monoamine compound and a bis-secondary diamine compound.

17. The epoxy resin composition of claim 15, wherein the amino molecule containing ≤2 N—H hydrogens is selected from the group consisting of monoethanolamine, diethanolamine, 3-aminopropanol, 2-aminopropanol, aminobenzylamine, aniline, p-anisidine, butylamine, piperazine, and N,N'-dimethylethylenediamine, tert-butylamine, sec-butylamine, 2-amino-2-methyl-1-propanol and combinations thereof.

18. The epoxy resin composition of claim 17, wherein the amino molecule containing ≤2 N—H hydrogens is monoethanolamine.

19. The epoxy resin composition of claim 17, wherein the amino molecule containing ≤2 N—H hydrogens is 3-aminopropanol.

20. The epoxy resin composition of claim 17, wherein the amino molecule containing ≤2 N—H hydrogens is 2-aminopropanol.

21. The epoxy resin composition of claim 17, wherein the amino molecule containing ≤2 N—H hydrogens is 2-amino-2-methyl-1-propanol.

22. The epoxy resin composition of claim 16, wherein the amino molecule containing ≤2 N—H hydrogens is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. % of the composition.

23. A method of altering the working time of a curable epoxy resin composition to compensate for ambient temperatures comprising:

forming a stable resin blend including a cross-linkable epoxy resin; selecting a cross-linking agent for the epoxy resin from the group consisting of a polyamine cross-linking agent comprising a compound having Formula (1):

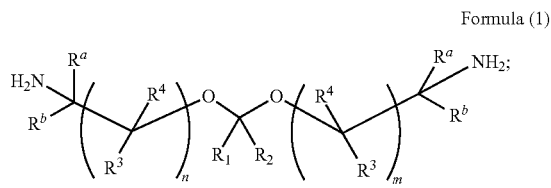

Formula (1)

wherein:

each of $R^1$ and $R^2$ is independently selected from the group consisting of hydrogen, alkyl group, cycloalkyl group and aromatic group; or $R^1$ and $R^2$ together with the carbon atom to which they are attached form a cycloalkyl group;

each of $R^3$ and $R^4$ is independently selected from the group consisting of hydrogen, alkyl group, cycloalkyl group and aromatic group; or $R^3$ and $R^4$ together with the carbon atom to which they are attached form a cyclic ring;

each $R^a$ and $R^b$ is independently selected from the group consisting of alkyl group, cycloalkyl group and aromatic group; and each m and n is independently an integer ranging from 0 to 20; and wherein the selection is made such that a mixture of the cross-linking agent and the epoxy resin has a long working time at or near ambient temperatures.

* * * * *